United States Patent [19]

Barnes et al.

[11] Patent Number: 5,506,211
[45] Date of Patent: Apr. 9, 1996

[54] GENISTEIN FOR USE IN INHIBITING OSTEROCLASTS

[75] Inventors: Stephen Barnes, Birmingham; Harry C. Blair, Mountain Brook, both of Ala.

[73] Assignee: The UAB Research Foundation, Birmingham, Ala.

[21] Appl. No.: 241,040

[22] Filed: May 9, 1994

[51] Int. Cl.$^6$ ............................................. A61K 31/70
[52] U.S. Cl. ........................... 514/27; 424/439; 424/441; 514/25; 514/456; 514/457
[58] Field of Search ................................. 424/439, 441; 514/456, 457, 25, 27

[56] References Cited

U.S. PATENT DOCUMENTS

| | | | |
|---|---|---|---|
| 4,163,746 | 8/1979 | Feuer et al. | 260/345.2 |
| 4,644,012 | 2/1987 | Tsuda et al. | 514/456 |
| 4,826,963 | 5/1989 | Stadler née Szoke et al. | 536/103 |
| 4,841,077 | 6/1989 | Ito et al. | 549/402 |
| 4,960,908 | 10/1990 | Ito et al. | 549/403 |
| 5,043,326 | 8/1991 | Stadler née Szoke et al. | 514/58 |
| 5,110,720 | 5/1992 | Csányi et al. | 433/215 |
| 5,424,331 | 6/1995 | Shlyankevich | 514/456 |

FOREIGN PATENT DOCUMENTS

| | | |
|---|---|---|
| WO91/14429 | 10/1991 | WIPO . |
| WO92/13538 | 8/1992 | WIPO . |
| WO93/23069 | 11/1993 | WIPO . |
| WO94/23716 | 10/1994 | WIPO . |

OTHER PUBLICATIONS

Akiyama et al., "Genistein, a Specific Inhibitor of Tyrosine-specific Protein Kinases," *The Journal of Biological Chemistry*, 262(12):5592–5595, 1987.

Brandi, M. L., "Flavonoids: biochemical effects and therapeutic applications," *Bone and Mineral* 19(suppl):S3–S14, 1992.

Breslau et al., "Relationship of Animal Protein-Rich Diet to Kidney Stone Formation and Calcium Metabolism," *Journal of Clinical Endocrinology and Metabolism*, 66(1):140–146, 1988.

Carano et al., "Bisphosphonates Directly Inhibit the Bone Resorption Activity of Isolated Avian Osteoclasts In Vitro," *J. Clin. Invest.*, 85:456–461, 1990.

Coward et al., "Genistein, Daidzein, and Their β–Glycoside Conjugates: Antitumor Isoflavones in Soybean Foods from American and Asian Diets," *Journal of Agricultural and Food Chemistry*, 41(11):1961–1967, 1993.

Davidai et al., "PGDF induces tyrosine phosphorylatin in osteoblast–like cells: relevance to mitogenesis," the American Physiological Society, E205–E209, 1992.

Fotsis et al., "Genistein, a dietary–derived inhibitor of in vitro angiogenesis," *Proc. Natl. Acad. Sci. USA*, 90:2690–2694, 1993.

Kallman, B., "Are You Aware? Put Some Soy In Your Life," *Let's Live*, p12, 1994.

Kalu et al., "Modulation of Age–Related Hyperparathyroidism and Senile Bone Loss in Fischer Rats by Soy Protein and Food Restriction," *Endocrinology*, 122(5):1847–1854, 1988.

Quarles et al., "Prostaglandin $F_{2\alpha}$–Induced Mitogenesis in MC3T3–E1 Osteoblasts: Role of Protein Kinase–C–Mediated Tyrosine Phosphorylation," *Endocrinology*, 132(4):1505–1513, 1993.

Schvartz et al., "Endothelin Rapidly Stimulates Tyrosine Phosphorylation in Osteoblast–Like Cells," *Peptides*, 13:159–163, 1992.

Yoneda et al., "Herbimycin A, a pp60$^{c-src}$ Tyrosine Kinase Inhibitor, Inhibits Osteoclastic Bone Resorption In Vitro and Hypercalcemia In Vivo," *J. Clin. Invest.*, 91:2791–2795, 1993.

Abstract from Japanese Patent, JP 5,170,756 (1993).

*Primary Examiner*—José G. Dees
*Assistant Examiner*—Barbara S. Frazier
*Attorney, Agent, or Firm*—Arnold, White & Durkee

[57] ABSTRACT

Disclosed are methods and compositions for use in inhibiting osteoclast activity and, particularly, the osteoclast acid secretion that leads to bone-degradation. It is shown that the isoflavone genistein inhibits the acid secretion of osteoclasts and reduces bone resorption. The present invention thus provides advantageous methods for use in inhibiting osteoclast activity, as may be employed to reduce bone loss, for example, in patients with osteoporosis, metastatic bone cancers and renal failure.

27 Claims, 23 Drawing Sheets

GENISTEIN FOR USE IN INHIBITING OSTEROCLASTS

The U.S. Government owns rights in the present invention pursuant to grant numbers 1R01 and CA61668 from the National Cancer Institute.

BACKGROUND OF THE INVENTION

1. Field of the Invention

The present invention relates generally to the fields of bone cells and also to isoflavones. Particularly, the invention concerns the discovery that the isoflavone genistein inhibits the acid secretion of bone-degrading cells termed osteoclasts. The invention thus provides methods and compositions for use in inhibiting osteoclast activity, as may be employed to reduce bone resorption.

2. Description of the Related Art

Metabolic bone disease is a common and economically important problem that affects many patients. Bone degradation often leads to osteoporosis, as well as bone lesions in metastatic cancer and other disease states. This degradation is mediated by cells of the osteoclast type. Current therapy for bone resorption is not very effective, which has led to an active pursuit of effective anti-osteoclastic drugs.

Candidate compounds to treat bone resorption include (1) gallium nitrate; (2) a large number of bisphosphonate derivatives; (3) certain antibiotics, such as herbimycin and plicamycin; (4) bone-binding antibiotics, principally tetracyclines; (5) protease inhibitors; (6) estrogen analogues or inhibitors such as raloxifene and tamoxifen; and (7) calcitonin and calcitonin congeners.

Each of the foregoing candidates suffer from independent sets of drawbacks that limit their effectiveness. Most notably perhaps, plicamycin (also known as mithramycin) has been shown to have fatal side effects. Also, gallium nitrate, bisphosphonate derivatives and bone-binding antibiotics all accumulate in the skeleton; herbimycin and protease inhibitors exhibit toxicity; estrogen analogues and inhibitors adversely affect hormone balance and sexual characteristics; and calcitonin and its relatives have yet to demonstrate meaningful effects.

It is thus clear that there is a significant need in the art for new compositions and methods by which to treat bone resorption and the many disease states that it causes or to which it contributes. The development of an anti-osteoclastic agent that exhibits low toxicity and has few side effects would represent a significant breakthrough, especially if such an agent was found to be readily available and could be administered orally.

SUMMARY OF THE INVENTION

The present invention seeks to overcome these and other drawbacks inherent in the prior art by providing new methods for use in reducing acid secretion by osteoclasts. The inventors discovered that the isoflavone genistein, found in soy products, effectively inhibits acid secretion and osteoclastic bone resorption. The invention thus provides methods for use in reducing bone resorption, as may be used to treat osteoporosis and other conditions involving bone loss, such as metastatic bone cancers.

To reduce osteoclastic acid secretion in accordance with the present invention, one would generally contact one or more osteoclasts with a composition that comprises a biologically effective amount of genistein. "Genistein" as used herein refers to the isoflavone compound as described in the Merck Index (7th Edition, 1960, p 474), or a derivative or analogue thereof that functions as a tyrosine kinase inhibitor. The ability of a genistein analogue to inhibit tyrosine kinase, and particularly, to inhibit $pp60^{src}$, may be readily determined by methods known to those of skill in the art, as described, for example in Akiyama et al. (1987), incorporated herein by reference.

The present invention thus encompasses the use of any genistein derivative that has a significant (i.e., consistently above background) inhibitory effect on tyrosine kinases. Also encompassed are genistein-derived compounds that may be formed upon ingestion. For example, genistein glucuronides, as for other glucuronides, are hydrolyzed by β-glucuronidases in the large bowel, and the unconjugated forms reabsorbed. In this environment the genistein compounds may undergo other chemical modifications, such as reduction to isoflavans or B-ring-opened forms, all such compounds are intended to fall within the scope of the present invention.

The term "a biologically effective amount", as used herein, refers to an amount of purified genistein, or an amount of a genistein-containing composition, that is effective to inhibit osteoclast acid secretion. As disclosed herein in Examples I, II and IV, and in FIGS. 1–4, genistein is effective at inhibiting osteoclast acid secretion at levels of less than 1 µM (0.27 µg/ml), with half maximal inhibition being achieved with at about ~2 µM, with a mean of about 3 µM (0.75 to 0.8 µg/ml). Therefore, amounts of purified genistein or genistein-containing compositions that result in local concentrations of genistein in approximately these ranges are "effective amounts".

Results from the cellular and bone resorption assay systems used herein are widely accepted in the art as predictive of in vivo effects. As the bone resorption assay uses material that includes all bone cells, it is an ex vivo assay. Thus, the showing that genistein inhibits bone resorption in these assays is evidence of the clinical utility of genistein for treating osteoporosis. Various scientific publications, such as Carano et al. (1990); Blair & Schlesinger (1992); Schlesinger & Blair (1992); Väänänen et al., 1990; all support the fact that such assays are accepted as being predictive of in vivo activity. Furthermore, the in vitro effects of Herbimycin A on bone resorption were shown to correlate with in vivo activity (Yoneda et al., 1993).

Although the advantageous results disclosed herein clearly teach that genistein has utility in the inhibition of bone resorption, and may thus be used to treat osteoporosis in humans, several other utilities are also apparent. These include veterinary uses, such as in horses and dogs, and particularly, the treatment of osteoporotic fractures in poultry, which poses a major problem in the egg production industry. Also, as genistein inhibits osteoclastic acid secretion, it may thus be used in vitro, for example, in connection with tissue culture methods and compositions for use in culturing bone tissues and cells.

In certain embodiments, osteoclasts located within an animal, such as a dog, horse, chicken or human subject, may be contacted with genistein, thereby inhibiting their activity and acid secretion in vivo. To achieve this, a purified genistein compound, or equally, a genistein-containing composition or food, would be administered to the animal. Any genistein-containing composition may be used to achieve in vivo effects, so long as it is in a pharmaceutically acceptable form. The phrases "pharmaceutically or pharmacologically acceptable" refer to molecular entities and compositions that do not produce an adverse, allergic or other untoward reaction when administered to a human.

Preparing genistein in a pharmaceutically acceptable form, or obtaining a genistein-containing composition that is pharmaceutically acceptable, does not pose a problem. In fact, it is an advantage of this invention that genistein is present within a variety of foodstuffs, particularly soy products, and that such foods, or concentrated forms thereof, may simply be ingested to provide an animal with an effective amount of genistein. Indeed, populations of Southeast Asians eat 70 mg of genistein per day without obvious ill effects (Soybean Utilization, Eds. Snyder & Kwon, p. 220). This is also a cost-effective method as isolated soy protein, containing about 450 mg of genistein per 450 gm (pound), can be bought cheaply. At current prices, a gram of genistein obtained within isolated soy protein in the U.S. costs approximately $3.75.

However, it is equally possible to provide genistein to an animal or human in a purified form, particularly a tablet. Therefore, genistein, or an inhibitory genistein derivative or analogue, may be obtained in a more purified form and administered to an animal, either orally, or via virtually any other route, such as intravenous injection. The formulation of genistein into a tablet is particularly preferred in certain embodiments, as this provides a simple means for ingesting genistein that is acceptable to the patient. Methods for purifying genistein are disclosed herein in Examples VI and VII. Also, synthetic genistein may be purchased from many commercial sources, such as, e.g., Gibco, L. C. Services and Upstate Biotechnology Incorporated (UBI).

Furthermore, owing to a present inventor's discovery that isoflavones in soy are present as malonylglucosides, it is proposed that such charged species may be advantageously purified using an anion exchange resin, rather than the previous purification methods that rely on differential solubility in aqueous alcohol and acetone solvents. The purification of malonylglucosides would result in the added benefit of directly providing one of the more preferred genistein conjugates.

Whether genistein is administered in a purified or semi-purified form, particularly a tablet, or is administered as part of an unmodified foodstuff, it is contemplated that preferred forms of genistein for use in treatment protocols will be those in which the isoflavone component is conjugated to an organic acid, such as the 6"-O-acetylglucosides and 6"-O-malonylglucosides. The reason for this is that the inventors have discovered that conjugated forms of genistein are absorbed in the large bowel and thus have advantageous biodistribution properties.

Certain methods for administering genistein to an animal or patient include giving the patient an ingestible soy food product. In general, any soy product may be used and, as prior heating does not affect the activity of genistein once absorbed, even those soy compositions that have been heated or otherwise processed, may be employed. These include products such as tofu, soy flour, soy protein concentrate, textured soy, soy milk and even meso.

However, from a bioavailability standpoint, the preferred soy products are those that have not been subjected to heat and, particularly, those that have not been heated in an aqueous alcoholic solvent. All such soy compositions have preserved the 6"-O-malonlyglucosides structures rather than destroying them. Examples of such compositions include unprocessed soy food products and isolated soy protein, obtainable from Protein Technologies International (St. Louis), and its derived products such as FIRST ALTERNATIVE™, a low-fat soy mil, and a low-fat tofu termed MORI-NU. Further examples are genistein conjugates that have been purified or semi-purified, or even synthesized, and formulated into a concentrated material, such as a tablet. Tablets that contain about the recommended daily genistein dose of between about 2–50 mg to 20–50 mg genistein, as described below, would be preferred, or ones that contain half or a third of such a dose, which would be taken two or three times a day.

This invention provides novel methods for reducing bone resorption in animals and human subjects that exhibit symptoms associated with bone resorption, for example, elderly people; patients known or suspected to have osteoporosis; patients known or suspected to have bone cancer or a cancer that has metastasized to the bone; patients with various hypercalcemias, whether or not associated with cancer; patients with Paget's disease; and patients with advanced or end-stage renal disease. The treatment methods of the invention generally comprise administering to such an animal or human subject a pharmaceutically acceptable genistein composition in an amount that is effective to reduce acid secretion by osteoclasts located within the animal. Suitable genistein compositions include all soy food products, and more preferably, those containing genistein in a conjugated form, such as unprocessed soy food products, those soy compositions isolated without significant heating, and also tablets or other concentrated forms of purified or synthetic genistein and genistein conjugates.

Amounts of genistein-containing compositions that are effective to reduce acid secretion by osteoclasts in vivo are also termed "pharmacologically effective amounts". The appropriate pharmacological doses of genistein (whether purified or present within a soy food) for use in treating osteoporosis, or other bone resorption disorders, may be determined from a consideration of the condition to be treated and the properties of the composition being administered. This will be readily understood by those of skill in the art when in possession of the present disclosure. For instance, in Example V, a detailed account of therapeutic doses and treatment methods is presented.

From a consideration of the data presented in Examples I through V, it is contemplated that to produce a sufficiently high (i.e., effective inhibitory) genistein concentration at the osteoclast, a daily intake of about 2–50 mg of genistein would be required for a human patient. More preferably, such doses would be between about 5–50 mg, about 10–50 mg, and most preferably, about 20–50 mg per person per day. These doses are contemplated to achieve 10–20% inhibition of osteoclasts. However, any inhibition between about 1% and about 10–30% would likely result in a clear benefit to the patient, hence the range in doses proposed.

Although the patient or animal would be closely monitored during treatment, it is not contemplated that significant adverse side effects or toxicity would result. The reasons for this include the fact that any over-inhibition of osteoclasts would likely be compensated for by the production of parathyroid hormone (PTH). As disclosed herein, the therapeutic margin for genistein is particularly good, with toxic effects not being observed until about a 30-fold excess over the half maximal inhibitory effects. Naturally, in clinical treatment, the patients would be closely monitored and doses adjusted by a physician, as is commonly practiced in the art. One would particularly take note of the patient's body weight, age, and health, as well as genistein uptake, genistein secretion, serum genistein levels and other factors well known to those in the medical arts, such as, e.g., liver function. One would also monitor bone density and bone turnover closely.

To treat other animals, such as dogs, horses or chickens, the weight of the animal would be determined and the dose adjusted accordingly. The above doses are calculated on the average weight of a human subject being around 60 to 65 to 70 kg, therefore suitable doses for other animals are easily determinable.

In terms of human treatment, certain suitable methods include administering from 2–50 mg to 20–50 mg of genistein in the form of a food product. This may be achieved by ingesting between about 2 g to 50 g, or about 20 to about 50 g, of soy isolated soy protein, per day per person. This daily intake of 20–50 mg of genistein could also be obtained from 2–40 or 20–40 g of unheated soy flours, soy protein concentrate, textured soy, or from 20–40 g of soy milk protein, with the provision that the weight of protein within the milk is probably about 10% of the weight of the milk itself. As the maximum limit for daily protein intake in the average person is about 100 g, the administration of more than this to a human patient is not recommended. An equally suitable treatment method is the administration of from 2–50 mg to 20–50 mg of genistein in the form of one or more tablets.

These treatment methods provide particularly advantages over those currently available for treating osteoporosis. For example, oral delivery rather than injection; the use of compounds that are naturally present in foods, rather than synthetic agents; avoiding excess use of antibiotics, such as herbimycin and tetracycline, that may contribute to the spread of antibiotic resistance; no or negligible toxicity; no or few side effects; and ready and cost-effective availability.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE PREFERRED EMBODIMENTS

Figure 1:
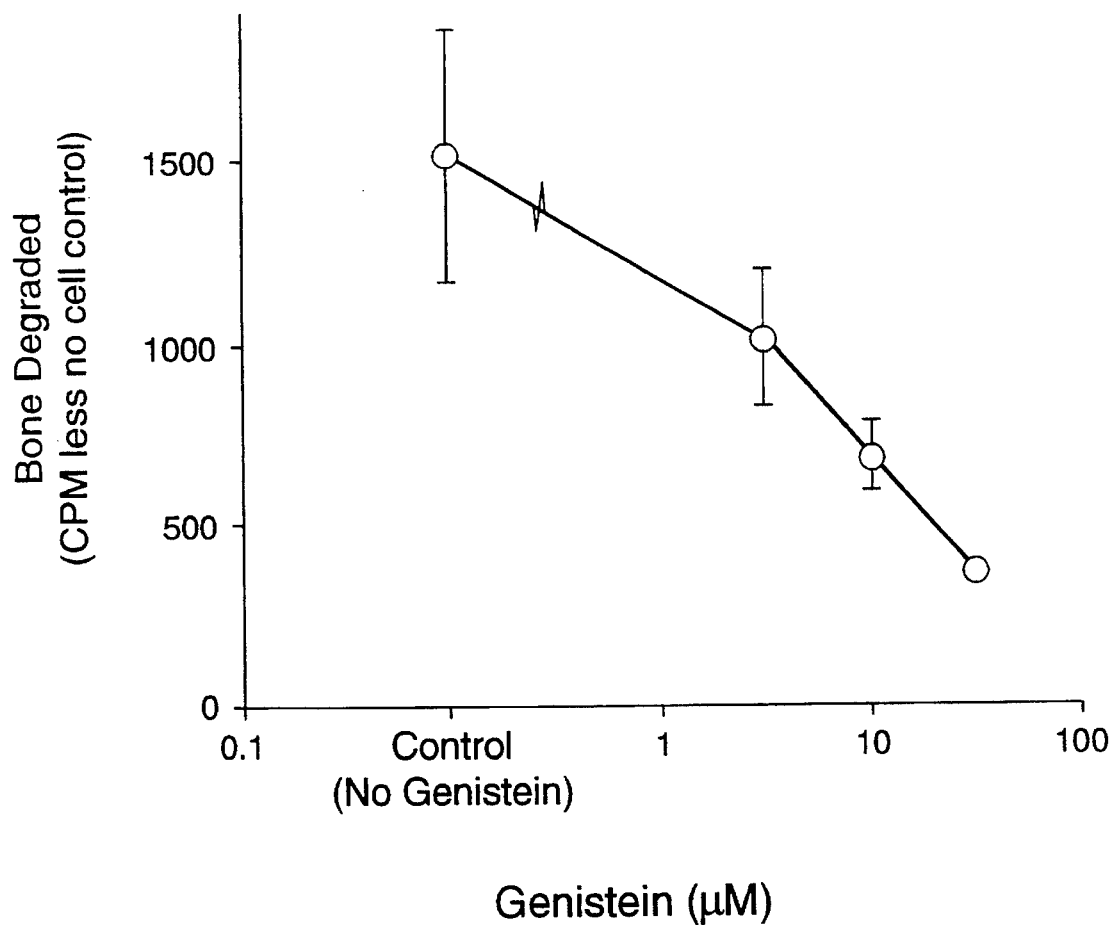
FIG. 1. Genistein inhibits osteoclastic bone degradation. Bone degradation assays were conducted as described in Example I. Genistein significantly inhibits bone degradation. Control note: the genistein congener dadzein, which is not an inhibitor of tyrosine kinases, has no effect on bone resorption at 10 μM, and inhibits ~10% at 30 μM.

Genistein, 5,7,4'-trihydroxyisoflavone, is one of the isoflavones found in soy. Certain reports have speculated on the presence of genistein and other isoflavones in soy oil or sauce, such as the abstract from the Japanese patent application JP 5170756. However, the present inventors have demonstrated that soy oil or sauce does not contain measurable, let alone isolatable, amounts of isoflavones, as described in Example VI, Table III, and in Coward et al. (1993).

This same report (JP Application 5170756) also suggests that 500 g of defatted soybeans can be extracted to yield 9.5 g of isoflavone aglucones at a purity of 90%. However, this figure is in marked contrast to the generally held belief in the art as to the quantity of isoflavones in soy products. For example, the present inventors have shown that the total isoflavone content of soy flour is about 2.7 mg/g, i.e., a maximum of about 1.35 g in 500 g, see Example VI and Coward et al. (1993). This is supported by other papers (e.g., Eldridge, 1982; Murphy, 1982) that give the isoflavone concentrations in soy as being between about 1 mg/g and about 3 mg/g.

Genistein is known to be a tyrosine kinase inhibitor (Akiyama et al., 1987) and has been proposed for use in treating several diseases and disorders, for example, cardiovascular disease, atherosclerosis and certain cancers (Carroll, 1992; reviewed in Messina et al., 1994; with a commentary by Kallman, 1994).

Preliminary data suggest soy products have certain effects on general bone health. For example, it has been suggested that soy protein diets assist in slowing renal function decline and progressive hyperparathyroidism (Kalu et al., 1988); that ingestion of vegetable protein may limit harmful calciuric responses (Breslau et al., 1988); and that flavenoids (although not isoflavenoids) are bone-anabolic, i.e., have effects on osteoblasts (Brandi, 1992). The abstract from the patent application WO 93/23069 also suggests that genistein may be used to treat adverse symptoms associated with menopause in women. This document, however, concentrates on the estrogen-like actions of genistein, referring to the treatment of breast cancer and pre-menstrual tension, and does not appear to mention osteoporosis.

Osteoclasts are macrophage derivatives uniquely dependent on activity of the tyrosine kinase oncogene c-src. This cell type mediates bone degradation that is responsible for osteoporosis, bone lesions in metastatic cancer and other disease states. The antibiotic Herbimycin A, which is a tyrosine kinase inhibitor, has been reported to inhibit osteoclastic bone resorption and hypercalcemia in vivo (Yoneda et al., 1993). It has been suggested that other cyclic antibiotics that inhibit $pp60^{c-src}$ may also inhibit osteoclastic bone resorption.

Although genistein is known to inhibit tyrosine kinases, it is chemically unrelated to Herbimycin A. It is also important to note that there have been articles published in the scientific literature that argue against the use of genistein in bone resorption. For example, in papers that concern the actions of genistein on bone tissues (Davidai et al., 1992; Quarles et al., 1993; Schvartz et al., 1992), genistein is shown to inhibit stimulators of osteoblast function. As osteoblasts, as opposed to osteoclasts, are bone-forming cells, this data indicates that genistein has an adverse effect on bone and suggests that genistein may even cause osteoporosis.

Despite suggestions to the contrary, the inventors contemplated that genistein may inhibit osteoclast activity and may prove useful in treating bone disorders. In testing the effects of genistein on osteoclasts, it was found that genistein was indeed able to inhibit osteoclast acid secretion, to alter the ability of osteoclasts to bind to bone, and to inhibit bone resorption. Thus, the present invention includes the use of genistein to reduce or prevent bone loss, such as in ageing (osteoporosis) and cancer progression (metastatic bone disease).

The data presented herein showing that genistein targets a central metabolic activity of the bone resorbing osteoclast by inhibiting acid secretion also suggests that genistein functions via a different mechanism to herbimycin. Herbimycin appears to primarily effect chloride conductivity in the ruffled border (specifically, its effect is partially reversed by by-passing chloride conductivity using the potassium ionophore valinomycin (2 µM) in the presence of potassium (120 mM). In contrast, genistein inhibits acid transport by a different mechanism that is not reversed by falinomycin under these conditions.

An isoflavone termed ipriflavone (7-isopropoxylisoflavone) has been used in clinical trials for the treatment of postmenopausal and senile osteoporosis. However, it is important to note that the active form in vivo is not known and that one of its metabolites, daidzein (4',7-dihydroxyisoflavone) has negligible activity in the osteoclast assay systems disclosed herein. Thus the use of genistein is distinct from the use of ipriflavone.

The present inventors, owing to a discovery relating to the various conjugated forms of genistein, also propose that certain genistein-containing compositions would be preferred for use in all therapeutic embodiments, including the treatment of disorders associated with bone resorption. As described below, for biodelivery purposes, the inventors prefer to use a soy composition that comprises genistein conjugated to an organic acid. It is an added advantage that the most preferred forms may be easily taken orally, as this overcomes one of the drawbacks inherent in current treatment strategies for osteoporosis, namely delivery via injection.

Except for heavily fermented soy-based foods such as miso, isoflavones in most of the common soy foods (soy milk, tofu, soy flour, soy protein concentrate and soy protein isolate) are present as glycosidic conjugates. However, the present inventors have found that in the unprocessed soybean hypocotyl and cotyledon, the isoflavones are found as β-glucosides (βGlc), 6-O"-malonylglucosides (6OMalGlc) and 6-O"-acetylglucosides (6OAcGlc). In the past, recovery of isoflavones from these food matrices has been carried out by Soxhlet extraction or by simple mixing with heated aqueous alcoholic solvents. In such extracts, the isoflavones were shown to be β-glucoside conjugates by HPLC and subsequent-mass spectrometry.

A more careful evaluation of the extraction conditions used for soy foods has revealed that (1) heating of the solvent is unnecessary for quantitative recovery and (2) heating in aqueous alcoholic solvents leads to de-esterification of 6OMalGlc conjugates to βGlc conjugates. At 80° C. for 2 hours, the deesterification is nearly complete. Soy foods, such as soy milk and tofu, which are prepared using a hot aqueous leaching step during their preparation contain mostly βGlc conjugates. In contrast, soy flours prepared by hexane extraction of crushed soybeans, contain mostly 6OMalGlc conjugates. Increasing use of heat in the preparation of soy flours led to increased, although small, amounts of the 6OAcGlc conjugates.

The present inventors have thus discovered that not all forms of soy contain the same chemical constituents. Furthermore, they have also discovered that soy foods are not necessarily of equivalent nutritional (or therapeutic) value. This is because the different conjugate forms have been discovered to have quite different routes of uptake, leading to different bioavailabilities and hence will likely have varying degrees of physiologic effectiveness.

In particular, the inventors have found that genistein, when conjugated to an organic acid, is not readily hydrolysed in the stomach and, hence, is not available for significant absorption in the small intestine (ileum). This means that this form of genistein is mainly absorbed through the large bowel. Evidence for this comes from the fact that following consumption of a product high in the 6"-O-malonylglucoside conjugates of isoflavones, the isoflavones are not detected in the urine or serum from 4–8 hours later, thus indicating that the principal site of intestinal absorption is the large bowel. On the other hand, consumption of a full-flat soy milk (containing β-glucoside conjugates only) led to the detection of isoflavones in the serum within 2 hours and in the 0–4 hr urine collection, suggesting that absorption occurs in this case from the small intestine.

In light of these data, the inventors propose that using soy compositions that have higher quantities of conjugated genistein, i.e., non heat-treated soy products or isolated soy protein, allows genistein bioavailability to be controlled and genistein to be targeted to the large bowel. This is envisioned to be of importance in treating bowel cancer, wherein the use of a soy composition high in conjugated genistein would be a significant advantage.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE I

GENISTEIN INHIBITS BONE RESORPTION

This example shows that genistein inhibits bone resorption. The assay systems used in Examples I and II include both cellular assays systems and also bone resorption assays that, as they contain all types of bone cells that are able to interact, essentially reflect ex vivo isolated organ type studies. Results from all of the assays used herein are widely accepted as being predictive of in vivo activity, as described in publications such as Carano et al. (1990), and in review articles, including Blair & Schlesinger (1992) and Schlesinger & Blair (1992).

1. Osteoclast Isolation and Culture

Arian osteoclasts were isolated from medullary bone of calcium-starved white leghorn laying hens, Gallus domesticus, essentially as described by Blair et al. (1986). Briefly, endosteum from laying hens fed a calcium deficient diet, in which osteoclasts are greatly increased and comprise approximately half the cell mass, was harvested, scraped into PBS, and sedimented through 70% newborn calf serum. 90–98% of cell mass of sedimenting material consists of osteoclasts or essentially inert red cells (Zambonin-Zallone et al., 1982; Blair et al., 1986). Although rich in osteoclasts, these preparations contain significant numbers of all other components of bone, including osteoblasts and marrow cells.

Cells were plated on glass cover slips in 3 cm petri plates for fluorescence studies, or 15 cm petri plates for Western Blots, or 24 well plates (2 cm$^2$/well) for resorption and binding studies. For resorption and binding studies, cells were plated at 5×10$^3$/well. Cells were maintained in α-MEM containing 5% fetal calf serum, 5% chicken serum, 100 μg/ml streptomycin and 100 units/ml penicillin at 37° C. in humidified air with 5% CO$_2$.

2. Bone Binding and Resorption Assays

Where bone was used, this was devitalized fragmented rat bone (Blair et al., 1986) sieved to sizes indicated, usually 25–50 μm. For studies of osteoclasts attached to bone or tissue culture plates, 100 μg unlabeled bone per 2 cm$^2$ well was used, or 5 mg per 10 cm plate. This amount of bone allowed 60–80% of multinucleated cells surviving 3 days to attach to bone fragments rather than plastic as assessed by phase-contrast microscopy.

Bone binding was determined by adherence of bone fragments to cultured cells (Carano et al., 1990). Briefly, this entailed adding labeled bone fragments to 3 day osteoclast cultures, incubating 4 h at 37° C. in a α-MEM with 5% fetal calf serum and 5% chicken serum, washing with PBS as 4 h, solubilizing the label overnight in 6N HCl, and scintillation counting.

Bone resorption was measured using [$^3$H]-proline labeled bone (Blair et al., 1986). Test compounds were added as 300 fold or greater concentrate in DMSO (dimethyl sulfoxide), and comparisons were relative to controls with the same vehicle added. Background and non-cell mediated degradation, typically 3–15% of cell mediated levels, determined using no-cell controls, is subtracted from reported values.

3. Results

The effect of genistein on bone resorption was determined using the bone resorption assay described above. It was found that the addition of genistein significantly inhibited bone resorption (FIG. 1). It should also be noted that the genistein congener dadzein, which is not an inhibitor of tyrosine kinases, has no effect on bone resorption at 10 μM and inhibits ~10% at 30 μM.

EXAMPLE II

GENISTEIN INHIBITS OSTEOCLAST ACTIVITY

This example shows that the genistein-mediated inhibition of bone resorption, described in Example I, is achieved via the inhibition of osteoclast activity. Osteoclastic resorption, such as that observed in the assays described in Example I, depends on acidic degradation, which in turn depends on calmodulin and tyrosine kinase dependent intracellular regulation. Therefore, the effects of genistein on osteoclastic cell membrane acid transport were next analyzed.

1. Osteoclast ruffled border acid transport

Osteoclast membrane vesicles were used for these studies. Cell fragmentation was by nitrogen cavitation, essentially as described by Blair et al. (1991). Briefly, 1×10$^7$ cells in 20 ml of lysis buffer (250 mM sucrose, 0.5 mM EDTA, 1 mM dithiothreitol, 10 mM Tris, pH 7.0) were disrupted by explosive decompression after 30 min at 40 atm N$_2$, 4° C. Centrifugation at 1000 ×g for 5 min and 4,700×6 for 10 min removed large cell fragments, nuclei, and mitochondria, and the vesicular fraction was obtained by pelleting at 49,999 ×g for 40 min. Cell-surface and vesicle acidification labeling showed that ~50% of membranes derived from these arian osteoclast preparations are ruffled border; cytoplasmic enzymes are <1% of whole cell levels in these preparations (Blair et al., 1991). H$^+$-ATPase is highly expressed in ruffled membrane, so that it prominently labels with antibody, while other medullary bone elements are essentially unreactive (Blair et al., 1989). Essential elements of this work are confirmed (Bekker, and Gay, 1990b; Väänänen et al., 1990).

For vesicle formation, membranes from 5×10$^6$ osteoclasts (~900 μg protein) were suspended in 120 ml mM KCl, 20 mM NaCl, 10 mM HEPES, pH 7.4 at 1.5 mg/ml protein at 4° C. Following vesicle formation, (30 min, 4° C.) preincubation was performed as described below in individual studies and Mg$^{2+}$-ATP dependent proton transport was determined using as the acid transport marker the fluorescent weak base acridine orange. Fluorescence spectrophotometry was performed using excitation at 468 nm, measuring emission at 540 nm (E540), in 2.5 ml of assay buffer mixture in 3 ml stirred quartz cuvettes at 37° C. (Blair et al., 1991) with digital fluorescence signal recording at 5 sec intervals. Assay buffer was 3 μM acridine orange, 1 mM ATP (or other concentration as specified), in 120 mM KCl, 20 mM NaCl, 10 mM HEPES, pH 7.40, to which 100 μg vesicle protein (25–45 μl of reconstituted vesicles) was added, followed by 2 mM $Mg^{2+}$ to initiate transport. Transport was determined as the initial rate of change of acridine fluorescence ($V_i$), or from the total change in fluorescence, 300 sec after initiation, by addition of 1 mM $NH_4Cl$ to wash out acridine accumulated in acidic vesicles (steady state, δ FU at 540 nm).

2. Results

Figure 2:
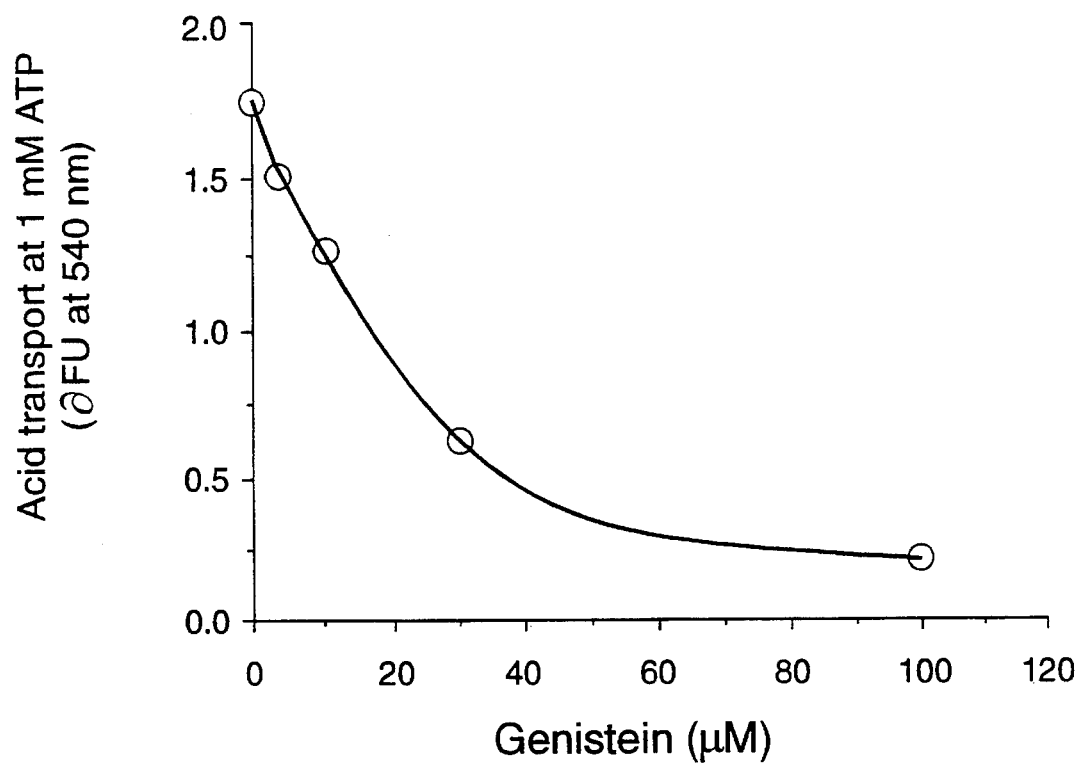
FIG. 2. Genistein inhibits osteoclast cell membrane acid transport. This figure shows that at doses comparable to those inhibiting bone resorption by whole cells, i.e., those shown in FIG. 1, osteoclast cell membrane acid transport is inhibited. Dadzein, a genistein congener that does not inhibit tyrosine kinases, was used as a control. It was found that dadzein has no effect on osteoclast acid transport at 10 μM and inhibits <20% at 30 μM.

Using the assay described above, it was found that at doses comparable to those inhibiting bone resorption by whole cells, osteoclast cell membrane acid transport is inhibited by genistein (FIG. 2). It was also found that the genistein congener dadzein, which is not an inhibitor of tyrosine kinases, has no effect on osteoclast acid transport at 10 μM and inhibits <20% at 30 μM.

Figure 4:
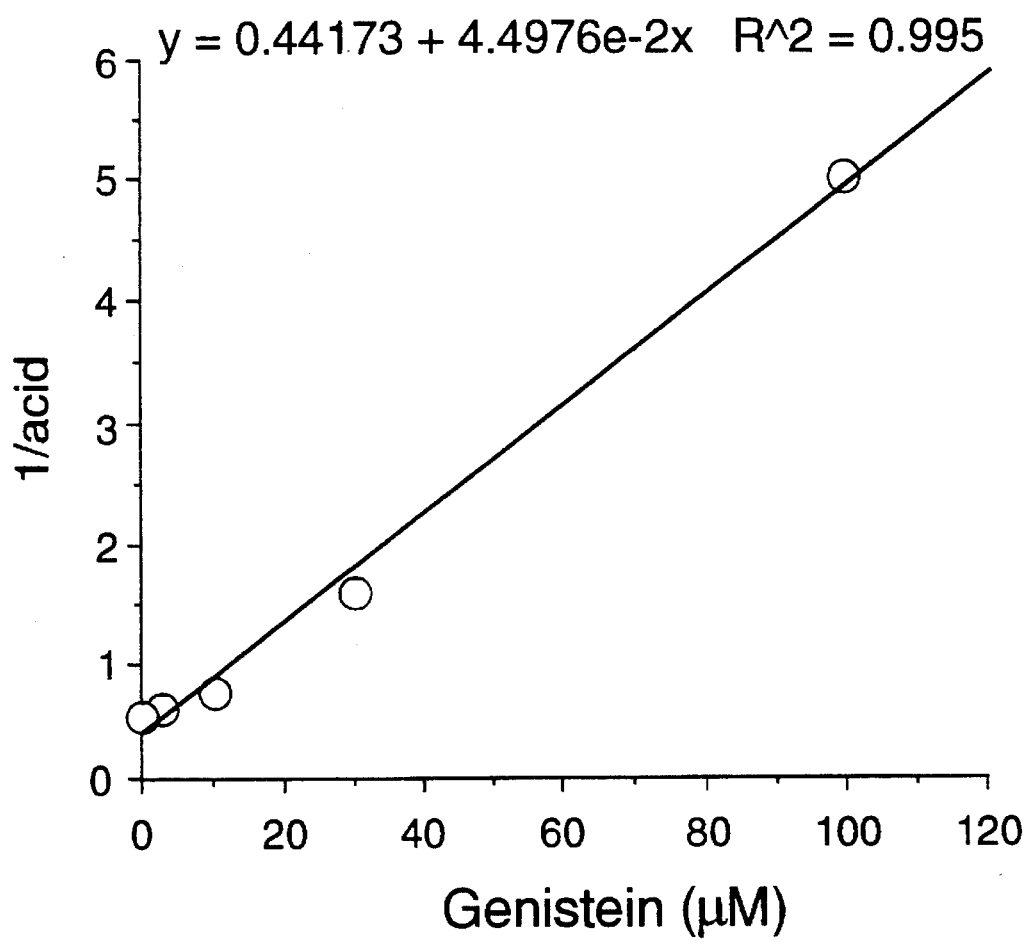
FIG. 4. Genistein inhibition of osteoclast acidification is proportional to the inhibitor concentration. This figure shows that osteoclast acidification is proportional to the inverse of the inhibitor concentration (thus more genistein results in less acid), suggesting that one important chemical interaction is involved.

Using the same assays used to generate the data in FIG. 2, it was also found that the effects of genistein on osteoclast acidification are proportional to the inverse of the inhibitor concentration (FIG. 4). This suggests that one important chemical interaction is involved.

EXAMPLE III

OSTEOCLAST RECOVERY AFTER GENISTEIN REMOVAL

In any method proposed for use in in vivo treatment protocols, an assessment of the potential toxicity is important. This example describes results of an assay indicating that toxicity of genistein is unlikely to be a problem in treating osteoporosis.

Figure 3:
FIG. 3. Osteoclasts survive after removal of genistein. The same methods were employed as those used to generate the data in FIG. 1. This figure shows that after exposure to moderate levels of genistein for 48 hours, functional osteoclasts may be recovered after genistein washout. It should be noted that at 30 μM genistein, cells die in 2–3 days.

Using the same methods as described in Example I and used to generate the data in FIG. 1, it was found that after a 48 hour incubation with moderate levels of genistein, osteoclasts could later be recovered after the genistein was washed out (FIG. 3). At 30 μM genistein, it was found that cells die in 2–3 days. Since advantageous effects are seen at 1 μM, with half maximal effects at 2–3 μM, toxicity at 30 μM indicates a broad therapeutic margin. Thus, unless about a 30-fold overdose was taken, toxicity would not likely pose a problem in clinical applications. It should also be noted that doses would not be designed to achieve 100%, or even 50%, inhibition as osteoclasts are vital cells. Thus, 10–20% inhibition would likely result in a clear benefit to the patient without significant side effects, particularly as over-inhibition would be compensated for by production of PTH.

Furthermore, evidence that toxicity is highly unlikely to be a significant problem comes from the fact that genistein is a naturally occurring compound in some foods and that populations of Southeast Asians eat 70 mg/day without obvious ill effects (Soybean Utilization, Eds. Snyder & Kwon, p.220).

EXAMPLE IV

COMPARATIVE EFFECTS OF GENISTEIN AND HERBIMYCIN

The present inventors found that substantial quantities of src co-isolate with osteoclast membrane vesicles and thus hypothesized that tyrosine kinase inhibitors might be active at the level of membrane transport. This example describes results from assays of tyrosine kinase inhibitors on avian osteoclast membrane HCl transport and osteoclastic activity in vitro.

The studies were conducted essentially as described in Example I. Membrane vesicles were produced by nitrogen cavitation and differential centrifugation, with acidification assayed by fluorescence quenching using 35 μg of membrane vesicle protein in 2.5 ml of 120 mM KCl, 20 mM NaCl, 10 mM HEPES pH 7.4, with 3 μM acridine orange and 1 mM ATP. Reaction was initiated by 2 mM $MgCl_2$, measuring 540 nm emission with fluorescence excitation at 468 nm.

It was found that, in addition to genistein, Herbimycin A also inhibited acid transport. Half maximal inhibition was found at ~10 μM for genistein and at about ~2 μM for Herbimycin A (but note that herbimycin is about ten times more toxic).

Addition of the potassium ionophore valinomycin, bypassing the requirement for Cl-conductivity in the 120 mM KCl solution used, restored acid transport activity in the presence of 5 μM herbimycin, suggesting that addition of this compound inactivates the chloride channel. In contrast, 20 μM genistein inactivated vesicles were valinomycin insensitive. Tyrphostin A47 (PDGF/EGF selective) was also inhibitory, with half maximal inhibition at 12 μM. Tyrphostin A25 (EGF/Insulin selective) and the control compounds daidzein (a genistein congener) and Tyrphostin A1 were inactive at 25 μM.

Bone resorption, measured in quadruplicate assays using 100 μg of $^3H$-proline labeled bone substrate and $10^4$ isolated arian osteoclasts, as described in Example I, showed that all of the tryphostins, including A47 and daidzein, were negative to >20 μM. Herbimycin and genistein were found to be inhibitory with half maximal effects at 0.3 to 0.5 μM and about 2 to about 3 μM, respectively. Essentially complete inhibition was noted at 3 days at 1 μM and 20 μM, respectively.

Despite the effective dose of herbimycin on osteoclast acid secretion being about 10 fold lower than that for genistein, the toxicity threshold for herbimycin is also about 10 fold lower, so these compounds appear to have similar therapeutic safety margins. This data comes from toxicity assays based upon cell recovery after herbimycin washout and on assays using $^3H$ leucine incorporation into cellular DNA.

EXAMPLE V

THE USE OF GENISTEIN TO STIMULATE BONE RESORPTION IN VIVO

From the data presented above, the inventors have determined that genistein inhibits osteoclast acid transport with half maximal inhibition at ~2–3 μM (a mean of about 3 μM); and that genistein inhibits bone resorption with half maximal effect at 10 μM, essentially being complete within 3 days at 20 μM. This data can be used with other known parameters to define the therapeutically effective ranges of genistein and soy products for use in treatment.

Adlercreutz et al. (1993) reported plasma total genistein concentrations as high as 0.1 μM in some vegetarian women; with genistein plasma levels of up to 1–4 μM in individuals on a high soy containing diet also being reported (Adlercreutz; Setchell; International Symposium on Phytoestrogens, 1993).

Reasonable estimates for the plasma level of genistein can be also be calculated from a consideration of dietary intake and rates of metabolism and excretion. A person consuming 35 g per day of soybeans (the average amount consumed by Taiwanese; Soyatech Survey 1991) has an intake of approximately 50 mg (185 μmol) of genistein, mostly in the conjugated form.

If a dose of 70 mg (259 μmoles) of genistein (in whatever form, unconjugated, i.e., isolated or synthesized, or conjugated, i.e., in a food matrix) is ingested per day by Southeast Asians and is fully absorbed, and if it is confined to the blood compartment (8 liters in the average person) and not metabolized or excreted, then the maximum possible blood concentration would be 32 μmoles/liter (23 μM).

However, genistein is relatively hydrophobic and will be taken up by cells—which must be accounted for. Previous studies on the tissue distribution of daidzein (Yueh & Chu 1977) have shown that in most tissues it is in similar concentrations to those in blood. Therefore, assuming that genistein equilibrates with total body water (56 liters), the equilibrium blood and tissue concentration would be a maximum of 4–5 μmoles/liter, and perhaps 3.3 μM. This value would be reduced by metabolism and excretion and be increased by repetitive daily dosing. Since there is no evidence that genistein has an extended half-life in the body, the effects of carry over from day-to-day are expected to be minimal and the 4–5 μmoles/liter level is unlikely to be exceeded at such doses.

It is also known that isoflavone concentrations in soy are between about 1 mg/g and about 3 mg/g (Eldridge, 1982; Murphy, 1982). Therefore, taking genistein concentration in soy protein foodstuffs as being a minimum of 1 mg per gram is a conservative estimate. Accordingly, the maximum daily delivery dose of genistein in the form of food is 80 mg in women and 100 mg in men (based on a protein intake of 80 g and 100 g per day for women and men). If genistein is administered separate from the soy food matrix or as a food product that is enhanced with respect to genistein, higher does levels can be achieved. It should also be noted here that the synthetic isoflavone, ipriflavone, is currently administered at a dose of 600 mg per person per day.

The low aqueous solubility of genistein (<50 μg per ml) should also be considered. This might result in a maximum total absorption independent of dose. However, by administering genistein mixed with the bile salt, sodium taurocholate (NaTC), its aqueous solubility can be substantially enhanced. The present inventors have used this delivery method for studies performed in rats. It was found that 40–50% of intestinally administered genistein appears in bile over a 4 hr period (this is also evidence of genistein undergoing and enterohepatic circulation). NaTC is a naturally occurring bile salt and may have a role in the absorption of genistein released from food.

Based on the data of the present inventors and the foregoing information, it is contemplated that to achieve a sufficiently high genistein concentration at the osteoclast (i.e., one capable of exerting an inhibitory effect on osteoclast activity and bone resorption) a daily intake of between about 2–50 mg and about 20–50 mg of genistein would be required. The difference in these figures is due to the range of inhibitory effects to be exerted on the osteoclast. It is not desirable to completely inhibit such cells, which have other important roles in the body. A 10–20% inhibition is contemplated to be a generally desirable goal.

Naturally, individual doses would be closely monitored and adjusted by an attending physician. One would particularly take note of the patient's body weight, genistein uptake, genistein secretion, age and other factors, such as, e.g., liver function, that are well known to those that conduct clinical trials and/or human treatment studies. In clinical use, the serum genistein levels would be monitored, as would bone density and bone turnover.

Daily doses of between about 2–50 mg, or 20–50 mg, of genistein would be provided by 2–40 or 20–40 g of isolated soy protein, or 2–40, or 20–40 g, of other soy foods, such as soy flours, soy protein concentrate, textured soy or soy milk protein (with the protein being about 10% of the weight of the milk). Certain preferred soy products are isolated soy protein, e.g., from Protein Technologies International (St. Louis), and its derived products, such as FIRST ALTERNATIVE™, a low-fat soy milk, and a low-fat tofu (MORI-NU™). Other preferred products are contemplated to be tablets comprising purified or synthetic genistein.

In animals it is possible to deliver approximately 30% by weight of the diet as soy protein. Therefore, rats eat approximately 12–15 g of diet per day (irrespective of age). This is 4–5 g of soy protein per day, or 4–6 mg per day of genistein (per 300 g adult rat). Although this cannot be extrapolated to humans in a linear manner, it can be seen that daily intakes of 20–50 mg of genistein, as provided by 20–50 g of isolated soy protein, are perfectly reasonable quantities (based upon an average human male being 70 kg). This is supported by known daily intakes of genistein, which are about 70 mg in certain Asian cultures (Soybean Utilization, Eds. Snyder & Kwon, p.220). Calculations of genistein doses for use in other animals would be straightforward based upon the weight of the animal and the data presented above.

EXAMPLE VI

GENISTEIN CONTENT OF SOY MATERIALS

The present example describes the extraction of isoflavones from soy products. Additional information may be found in Coward et al. (1993), incorporated herein by reference. This protocol is directly related to the generation of the data presented in Tables I through III.

Isoflavones in solid foods (analyzed in triplicate), to which 1.25 mg of fluorescein was added as an internal standard, were extracted into 80% aqueous methanol (10 mL/g) by stirring 1 h at 60° C. The other soy products (miso, soy milk, soy paste, and tofu) were extracted whole and also after freeze drying. The mixture was centrifuged (10 min at 2500 g) and the supernatant decanted into a round-bottom flask. The pellet was resuspended in 80% aqueous methanol (2×5 mL) and centrifuged, and the supernatants were combined and taken to dryness using a rotary evaporator. The dried extracts were then redissolved in 50% aqueous methanol (5 mL), and lipids were removed and discarded by partitioning into hexane (4×20 mL). The aqueous methanol phase was evaporated to dryness on a rotary evaporator and the dried residue dispersed in 10 mL of 80% aqueous methanol. An aliquot of the mixture was centrifuged at 14000 g for 2 min in an Eppendorf microfuge just prior to analysis by HPLC. Tables I, II and III show the isoflavone concentrations of soy materials, products and foods.

TABLE I

Isoflavone Concentrations[a] in Asian Primary Soy Materials

| food | basis | conjugated | | aglucones | | total | D/G ratio | aglucones, % | |
|---|---|---|---|---|---|---|---|---|---|
| | | genistin | daidzin | genistein | daidzein | | | genistein | daidzein |
| soy milk | g | 0.130 ± 0.004 | 0.103 ± 0.006 | 0.007 ± 0.000 | 0.011 ± 0.002 | 0.252 ± 0.012 | | | |
| | g dry wt | 1.680 ± 0.060 | 1.337 ± 0.087 | 0.098 ± 0.002 | 0.141 ± 0.019 | 3.256 ± 0.168 | 0.83 | 5 | 10 |
| tofu[b] | g | 0.249 ± 0.028 | 0.121 ± 0.010 | 0.031 ± 0.001 | 0.016 ± 0.001 | 0.417 ± 0.036 | | | |
| | g dry wt | 1.215 ± 0.137 | 0.591 ± 0.046 | 0.151 ± 0.006 | 0.0077 ± 0.005 | 2.031 ± 0.171 | 0.49 | 11 | 12 |
| tofu[c] | g | 0.269 ± 0.004 | 0.200 ± 0.008 | 0.015 ± 0.001 | 0.015 ± 0.000 | 0.494 ± 0.011 | | | |
| | g dry wt | 2.087 ± 0.030 | 1.513 ± 0.019 | 0.116 ± 0.004 | 0.113 ± 0.000 | 3.827 ± 0.045 | 0.74 | 5 | 7 |
| soy flour | g | 0.741 ± 0.100 | 0.582 ± 0.077 | 0.015 ± 0.002 | nd | 1.338 ± 0.178 | 0.77 | 2 | 0 |
| soy powder | g | 1.148 ± 0.103 | 0.582 ± 0.054 | 0.014 ± 0.001 | nd | 1.748 ± 0.156 | 0.50 | 1 | 0 |
| soy nuts | g | 1.390 ± 0.039 | 0.853 ± 0.022 | 0.066 ± 0.001 | 0.054 ± 0.001 | 2.363 ± 0.061 | 0.62 | 5 | 6 |

[a]mg/g; mean ± 1 SD of triplicate analyses.
[b]Tree of Life tofu.
[c]Mori-Nu tofu.

TABLE II

Isoflavone Concentrations[a] in Processed or Fermented Asian Soy Products

| soy product | basis | conjugated | | aglucones | | total | D/G ratio | aglucones, % | |
|---|---|---|---|---|---|---|---|---|---|
| | | genistin | daidzin | genistein | daidzein | | | genistein | daidzein |
| tempeh | g | 0.113 ± 0.028 | 0.040 ± 0.013 | 0.164 ± 0.004 | 0.113 ± 0.007 | 0.430 ± 0.005 | | | |
| | g dry wt | 0.296 ± 0.063 | 0.103 ± 0.029 | 0.434 ± 0.005 | 0.298 ± 0.009 | 1.130 ± 0.096 | 0.55 | 59 | 74 |
| miso | g | 0.043 ± 0.004 | 0.035 ± 0.025 | 0.497 ± 0.029 | 0.345 ± 0.013 | 0.920 ± 0.070 | | | |
| | g dry wt | 0.064 ± 0.007 | 0.054 ± 0.038 | 0.745 ± 0.068 | 0.516 ± 0.036 | 1.379 ± 0.149 | 0.70 | 92 | 91 |
| rice miso | g | 0.198 ± 0.011 | 0.000 ± 0.000 | 0.136 ± 0.000 | 0.071 ± 0.002 | 0.404 ± 0.009 | | | |
| | g dry wt | 0.353 ± 0.018 | 0.000 ± 0.000 | 0.242 ± 0.001 | 0.127 ± 0.003 | 0.721 ± 0.014 | 0.21 | 41 | 100 |
| barley miso | g | 0.155 ± 0.020 | 0.142 ± 0.025 | 0.239 ± 0.008 | 0.185 ± 0.007 | 0.721 ± 0.053 | | | |
| | g dry wt | 0.258 ± 0.032 | 0.235 ± 0.042 | 0.396 ± 0.012 | 0.306 ± 0.009 | 1.195 ± 0.084 | 0.83 | 61 | 57 |
| Shiromiso soup mix | g | 0.267 ± 0.020 | 0.163 ± 0.028 | 0.170 ± 0.006 | 0.108 ± 0.008 | 0.708 ± 0.059 | 0.62 | 39 | 40 |
| Akamiso soup mix | g | 0.319 ± 0.025 | 0.254 ± 0.044 | 0.173 ± 0.005 | 0.136 ± 0.008 | 0.882 ± 0.080 | 0.79 | 35 | 35 |
| soybean paste | g | 0.078 ± 0.014 | 0.044 ± 0.040 | 0.251 ± 0.008 | 0.197 ± 0.009 | 0.570 ± 0.071 | | | |
| | g dry wt | 0.160 ± 0.030 | 0.090 ± 0.081 | 0.514 ± 0.016 | 0.404 ± 0.019 | 1.168 ± 0.146 | 0.73 | 76 | 82 |
| soybean paste/rice | g | 0.066 ± 0.029 | 0.085 ± 0.016 | 0.108 ± 0.004 | 0.103 ± 0.006 | 0.362 ± 0.041 | | | |
| | g dry wt | 0.106 ± 0.045 | 0.136 ± 0.026 | 0.174 ± 0.008 | 0.166 ± 0.008 | 0.582 ± 0.061 | 1.08 | 62 | 55 |
| soybean paste/ wheat | g | 0.110 ± 0.008 | 0.094 ± 0.026 | 0.124 ± 0.014 | 0.105 ± 0.001 | 0.433 ± 0.032 | | | |
| | g dry wt | 0.220 ± 0.015 | 0.189 ± 0.052 | 0.248 ± 0.028 | 0.210 ± 0.003 | 0.867 ± 0.063 | 0.85 | 53 | 53 |

[a]Expressed as mg/g wet weight or mg/g dry weight; mean ± 1 SD of triplicate analyses. nd, not detected.

TABLE III

Isoflavone Concentrations[a] in Other Soy Foods

| soy food | basis | conjugated | | aglucones | | total | D/G ratio | aglucones, % | |
|---|---|---|---|---|---|---|---|---|---|
| | | genistin | daidzin | genistein | daidzein | | | genistein | daidzein |
| soy sauce | g | nd | nd | 0.009 ± 0.002 | 0.014 ± 0.001 | 0.023 ± 0.003 | | | |
| | g dry wt | nd | nd | 0.036 ± 0.014 | 0.054 ± 0.013 | 0.090 ± 0.026 | 1.50 | 100 | 100 |
| soy cheese | g | 0.028 ± 0.001 | 0.021 ± 0.001 | 0.002 ± 0.001 | 0.001 ± 0.001 | 0.050 ± 0.003 | | | |
| | g dry wt | 0.057 ± 0.001 | 0.043 ± 0.001 | 0.005 ± 0.001 | 0.001 ± 0.002 | 0.105 ± 0.003 | 0.71 | 8 | 2 |
| Tofutti | g | 0.022 ± 0.001 | 0.004 ± 0.006 | 0.004 ± 0.000 | 0.001 ± 0.002 | 0.032 ± 0.008 | | | |
| | g dry wt | 0.064 ± 0.001 | 0.012 ± 0.016 | 0.014 ± 0.001 | 0.003 ± 0.004 | 0.092 ± 0.020 | 0.19 | 18 | 20 |
| Ice Bean | g | 0.060 ± 0.006 | 0.055 ± 0.007 | 0.001 ± 0.000 | 0.001 ± 0.002 | 0.117 ± 0.014 | | | |
| | g dry wt | 0.184 ± 0.016 | 0.167 ± 0.022 | 0.004 ± 0.002 | 0.004 ± 0.006 | 0.360 ± 0.004 | 0.91 | 2 | 2 |

[a]Expressed as mg/g wet weight or mg/g dry weight; mean ± 1 SD of triplicate analyses. nd, not detected.

EXAMPLE VII

CONDITIONS FOR EXTRACTING GENISTEIN FROM SOY PRODUCTS

The present example indicates that, in the preparation of isoflavones from soy products, extraction with 80% aqueous methanol at room temperature was just as efficient as extraction at 60°–80° C. It also shows that heated extraction causes changes in isoflavone composition and that heating should be avoided.

A. Materials and Methods

1. Materials

Soy beans and EdenSoy soy milk were obtained from a National food store chain specializing in vegetable products. Hypocotyls were separated from the cotyledons by hand. Defatted soy flour and an isolated soy protein (Supro™) were obtained from Protein Technologies International, St. Louis, Mo. Soy molasses and toasted soy flour were obtained from the Archer Daniels Midland Co., Decatur, Ill., and tofu from Morinaga Nutritional Foods, Inc., Torrance, Calif.

HPLC grade methanol and acetonitrile and the disodium salt of fluorescein were used without further purification. Double distilled water used was filtered through a 0.45 μm pore size Superpore nylon membrane.

2. Extraction of isoflavones from soy foods

Daidzein and genistein and their β-glucoside conjugates were isolated and purified as described above in Example V, and in Coward et al. (1993); incorporated herein by reference. Briefly, portions of soy material (500 mg) were mixed with either 4 ml of 80% aqueous methanol or 80% aqueous acetonitrile-0.1% HCl (v/v) and the internal standard fluorescein (1 mg, as a concentrate in the same solvent) added to each. The mixtures were then placed in a tumbling mixer for 1, 2 and 24 h at room temperature (22° C). A second set of samples were extracted at 60° C. in a water bath for 1, 2 and 4 h. Aliquots of each mixture were clarified by centrifugation at 14,000 ×g in an Eppendorf centrifuge prior to reversed-phase HPLC analysis. In another set of studies, extraction was carried out at 80° C. for periods up to 4 hours.

3. HPLC analysis

Reversed-phase HPLC analysis of isoflavones was carried out on a 25 cm×4.6 mm Aquapore $C_8$ column (Applied Biosystems, Foster City, Calif.). Elution was carried out at a flow rate of 1.5 ml/min using a solvent gradient consisting of a linear increase from 0–50% of acetonitrile (solvent B) in water in a background of either 0.1% trifluoroacetic acid or 2 or 10 mM ammonium acetate (solvent A) over periods ranging from 10–30 min, followed by 100% solvent B for 5 min. The column was equilibrated in solvent A prior to chromatography. Eluted isoflavones were detected by their absorbance at 262 nm. Quantitative data for daidzein, daidzin, genistein and genistin were obtained by comparison to known standards.

As the molar extinction coefficients of the daidzein and genistein 6OMalGlc conjugates approximate to those of daidzin and genistin, respectively (Kudou et al., 1991), the concentrations of the 6OMalGlc and the 6OAcGlc conjugates were calculated from standard curves for the corresponding β-glucoside. Similarly, concentrations of glycitein were calculated from the daidzein standard curve, and the concentrations of the glycitein 6OMalGlc and the 6OAcGlc conjugates from the daidzin standard curve.

4. Mass spectrometry analysis

Analyses were performed on an API III triple quadrupole mass spectrometer (PE-Sciex, Thornhill, Ontario, Canada) equipped with two Macintosh Quadra 950 computers for data analysis. The isoflavones in the soy extracts were separated by reversed-phase HPLC on a 10 cm×4.6 mm Aquapore $C_8$ column at a flow rate of 1.0 ml/min using a linear 0–50% gradient of acetonitrile (5% per min) in 0.1% acetic acid or 10 mM ammonium acetate. Positive and negative ions from eluted solutes were introduced into the mass spectrometer following their generation by atmospheric pressure chemical ionization caused by a corona discharge needle in the heated nebulizer interface of this instrument.

Isoflavone conjugates were also separated by reversed-phase HPLC on a 10 cm×2.1 mm Aquapore $C_8$ column at a flow rate of 0.2 ml/min, using a 0–50% acetonitrile gradient (5% per min) in aqueous 2 mM ammonium acetate. The column eluate was split 1:1, with 100 ml/min going to the IonSpray™ interface. Positive and negative ion mass spectra were recorded in this mode, with orifice potentials of 70 V and −60 V, respectively.

B. Results

1. Extraction conditions

Maximum recovery of the isoflavones from soy milk and the isolated soy protein with 80% aqueous methanol'sufficient for reproducible quantitative measurements was obtained by tumbling for 2 hours (Tables IV and V). Furthermore, for both soy products, there were no significant differences in overall recovery of isoflavones when extraction was performed at room temperature as opposed to 60° C. (Tables IV and V). Coefficients of variation obtained using the method described declined as the total isoflavone content rose (5.8%, 2.8%, and 1.6% for soy milk 2, soy milk 1 and isolated soy protein, respectively). In addition, no differences were detected between the use of 80% aqueous methanol and 80% aqueous acetonitrile containing 0.1% HCl for the 2 h room temperature extraction of the total isoflavones in toasted soy flour.

Figure 5A:
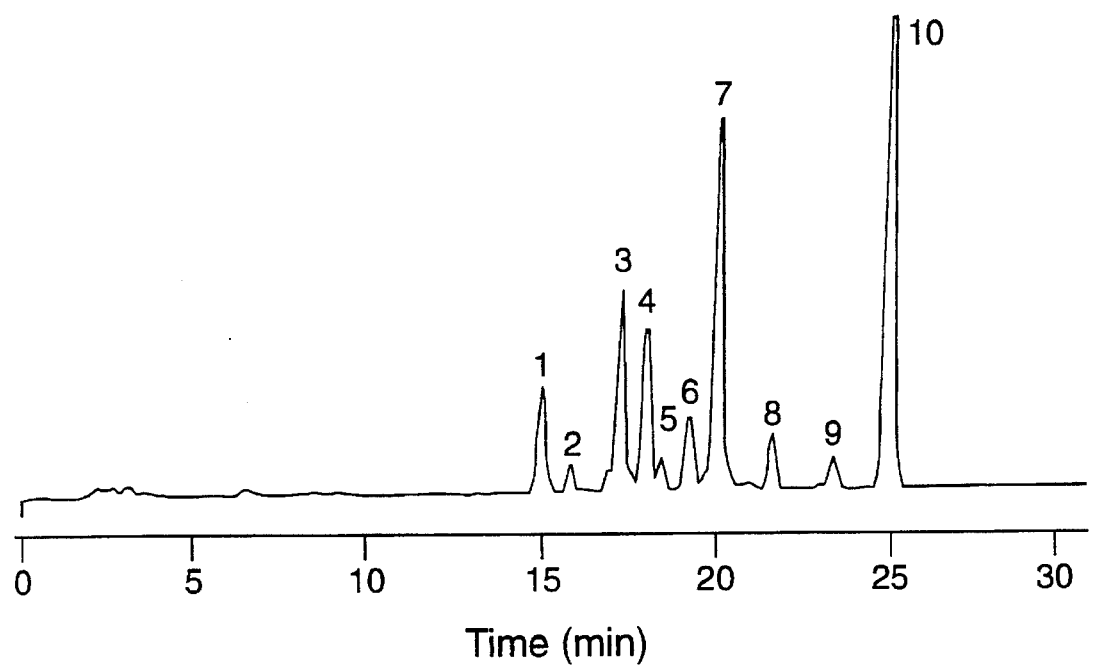
FIGS. 5A and 5B. Reversed-phase HPLC analysis of isoflavones in soy protein isolate extracted with 80% aqueous methanol at room temperature (A), or at 80° C. for 4 h (B). Peak identification: 1=dadzin, 2=glycitin, 3=genistin, 4=daidzein 6-OMalGlc, 5=glycitein 6-OMalGlc, 6=daidzein 6-OAcGlc, 7=genistein 6-OMalGlc, 8=genistein 6-OAcGlc, 9=genistein, 10=fluorescein internal standard. Analyses were performed on a 25 cm×4.6 mm $C_8$ Aquapore column using a linear elution gradient of 0–50% acetonitrile in 0.1% trifluoroacetic acid over 30 min at a flow rate of 1.5 ml /min. Isoflavones were detected by their absorbance at 262 nm.
Figure 5B:
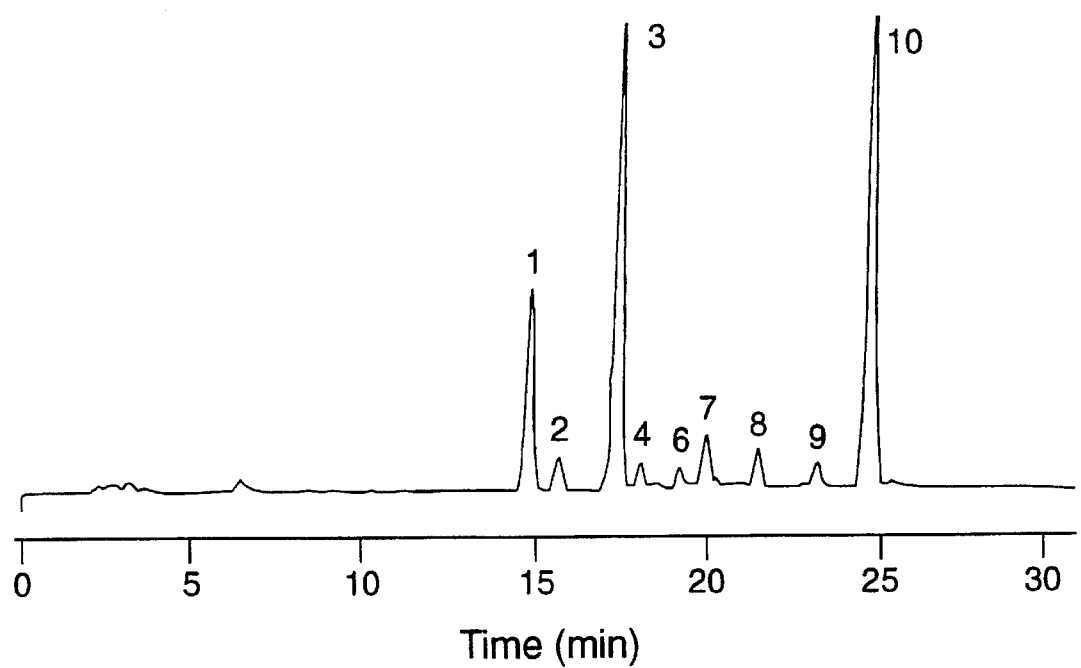
Figure 6A:
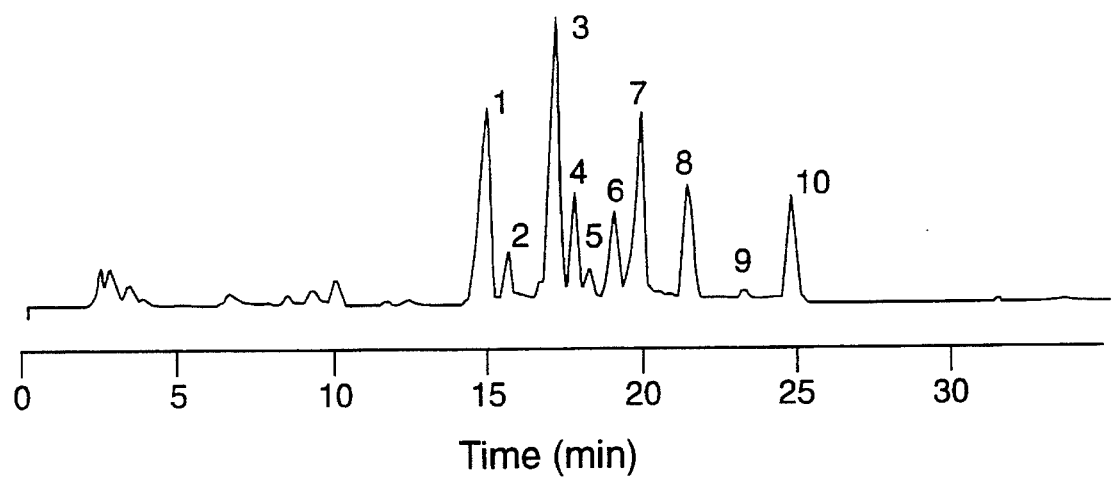
FIGS. 6A and 6B. Reversed-phase HPLC analysis of isoflavones extracted from toasted soy flour with 80% aqueous methanol at room temperature for 2 hours (A) and at 80° C. for 4 hours (B).
Figure 6B:
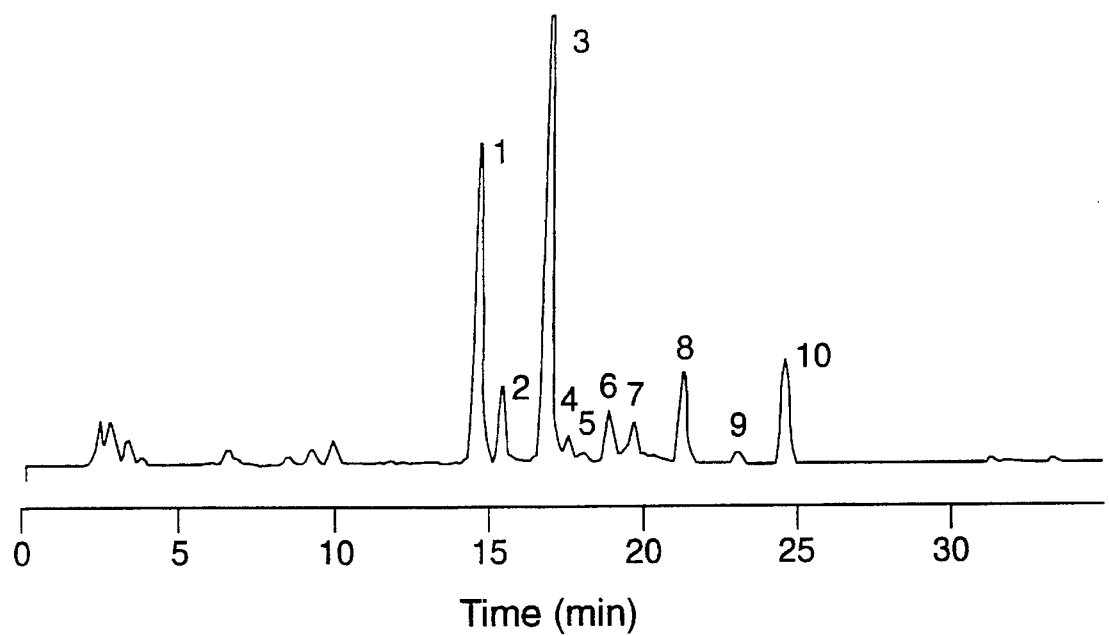

In the case of the soy milks, the isoflavones were present in the extracts almost entirely as their β-glucoside conjugates whether extracted at room temperature or at 60° C. In contrast, for the isolated soy protein, although extraction at 60° C. did not change the total isoflavone concentration, it did cause significant changes in the composition of the isoflavone conjugates. At each time point in the extraction, genistin and genistein concentrations were increased at the expense of genistein 6-OMalGlc (Table V). Similar trends were also observed for daidzin, daidzein and daidzein 6-OMalGlc. When the extraction temperature was increased to 80° C., the conversion of the isoflavone 6-OMalGlc conjugates to the β-glucoside conjugates was much greater and was time-dependent (FIG. 5). Heated extraction of toasted soy flour at 80° C. in 80% aqueous methanol also led to conversion of isoflavone 6-OAcGlc conjugates to their β-glucoside conjugates (FIG. 6). Even when kept at room temperature, isoflavones in 80% aqueous methanol extracts of the soy materials were converted gradually from the 6-OMalGlc forms to the β-glucosides.

The use of acetic acid in the HPLC mobile phase did not lead to a significant improvement in resolution of the isoflavone conjugates compared to trifluoroacetic acid. When ammonium acetate was included in the aqueous buffer (as used for analysis by HPLC-MS), the elution volumes of the isoflavone 6-OMalGlc conjugates decreased sharply due to ionization of their carboxyl groups.

TABLE IV

Effect of mixing time and heat on the extraction of isoflavones (μg/gm)* from soy milks

| | Room temperature | | | 60° C. | | |
|---|---|---|---|---|---|---|
| | 1 h | 2 h | 24 h | 1 h | 2 h | 4 h |
| Soy milk #1 | | | | | | |
| Daidzin | 89.4 ± 3.2 | 87.0 ± 0.9 | 83.7 ± 4.8 | 86.2 ± 1.4 | 87.2 ± 0.3 | 88.6 ± 1.1 |
| Daidzein | 3.7 ± 0.4 | 3.3 ± 0.4 | 2.6 ± 0.2 | 3.8 ± 1.1 | 3.1 ± 0.4 | 3.0 ± 0.4 |
| Genistin | 143 ± 2.6 | 138 ± 1.9 | 135 ± 6.3 | 140 ± 2.0 | 138 ± 1.4 | 139 ± 0.4 |
| Genistein 6-OMalGlc | 35.5 ± 1.6 | 35.1 ± 1.6 | 31.9 ± 1.8 | 31.4 ± 1.5 | 30.9 ± 1.5 | 29.1 ± 1.4 |
| Genistein | 3.4 ± 0.8 | 3.6 ± 0.4 | 2.8 ± 0.3 | 5.4 ± 1.6 | 3.2 ± 0.4 | 3.1 ± 0.6 |
| Glycitin | 7.9 ± 1.2 | 7.7 ± 0.5 | 7.0 ± 0.8 | 7.6 ± 0.5 | 8.4 ± 0.1 | 8.3 ± 0.8 |
| Total | 283 ± 11 | 274 ± 5 | 263 ± 17 | 275 ± 7 | 271 ± 3 | 271 ± 3 |
| Soy milk #2 | | | | | | |
| Daidzin | 52.2 ± 2.9 | 53.2 ± 4.4 | 52.4 ± 0.9 | 50.2 ± 0.8 | 50.8 ± 2.1 | 50.3 ± 2.6 |
| Daidzein | 2.1 ± 0.9 | 1.2 ± 0.9 | .9 ± 0.8 | 1.6 ± 0.9 | 0.7 ± 0.9 | n.d. |
| Genistin | 80.2 ± 2.6 | 81.0 ± 4.8 | 80.1 ± 0.6 | 78.4 ± 1.9 | 78.9 ± 1.6 | 82.9 ± 5.7 |
| Genistein 6-OMalGlc | 12.3 ± 1.4 | 13.5 ± 3.5 | 12.4 ± 2.8 | 10.8 ± 0.3 | 14.1 ± 3.2 | 13.0 ± 0.9 |
| Genistein | 1.5 ± 0.6 | 1.5 ± 0.3 | 1.3 ± 0.2 | 0.8 ± 0.6 | 1.9 ± 0.5 | 1.2 ± 0.1 |
| Glycitin | 9.6 ± 1.4 | 10.0 ± 1.5 | 9.9 ± 1.2 | 8.7 ± 0.2 | 9.1 ± 1.0 | 9.2 ± 1.0 |
| Total | 158 ± 11 | 160 ± 16 | 157 ± 4 | 150 ± 3 | 155 ± 9 | 156 ± 11 |

*Mean ± SD of triplicate measurements

TABLE V

Effect of mixing time and heating to 60° C. on the extraction of isoflavones (μg/gm)* from a soy protein isolate

| | Room temperature | | | 60° C. | | |
|---|---|---|---|---|---|---|
| Isoflavone | 1 h | 2 h | 24 h | 1 h | 2 h | 4 h |
| Daidzin | 275 ± 6 | 272 ± 9 | 297 ± 5 | 297 ± 2[a] | 309 ± 8[b] | 326 ± 2[c] |
| Daidzein 6-OMalGlc | 374 ± 9 | 361 ± 6 | 357 ± 4 | 344 ± 4[a] | 328 ± 5[b] | 318 ± 8[c] |
| Daidzein 6-OAcGlc | 93 ± 5 | 95 ± 4 | 92 ± 1 | 94 ± 3 | 93 ± 4 | 93 ± 2 |
| Daidzein | 52 ± 4 | 59 ± 5 | 57 ± 2 | 56 ± 11 | 66 ± 4 | 64 ± 4 |
| Genistin | 462 ± 9 | 460 ± 16 | 503 ± 10 | 512 ± 4[a] | 536 ± 7[b] | 571 ± 5[c] |
| Genistein 6-OMalGlc | 752 ± 16 | 762 ± 4 | 735 ± 17 | 707 ± 6[a] | 684 ± 13[b] | 654 ± 15[c] |
| Genistein 6-OAcGlc | 141 ± 8 | 142 ± 5 | 142 ± 4 | 140 ± 1 | 143 ± 6 | 148 ± 4 |
| Genistein | 49 ± 6 | 46 ± 9 | 43 ± 3 | 56 ± 8[a] | 59 ± 3[b] | 55 ± 8[c] |
| Glycitin | 86 ± 5 | 93 ± 12 | 95 ± 9 | 91 ± 1 | 97 ± 3 | 97 ± 1 |
| Glycitein | 82 ± 3 | 85 ± 1 | 75 ± 5 | 81 ± 3 | 75 ± 5 | 68 ± 2 |
| 6-OMalGlc Total | 2366 ± 66 | 2374 ± 48 | 2395 ± 9 | 2285 ± 26 | 2390 ± 37 | 2396 ± 28 |

Figure 7A:
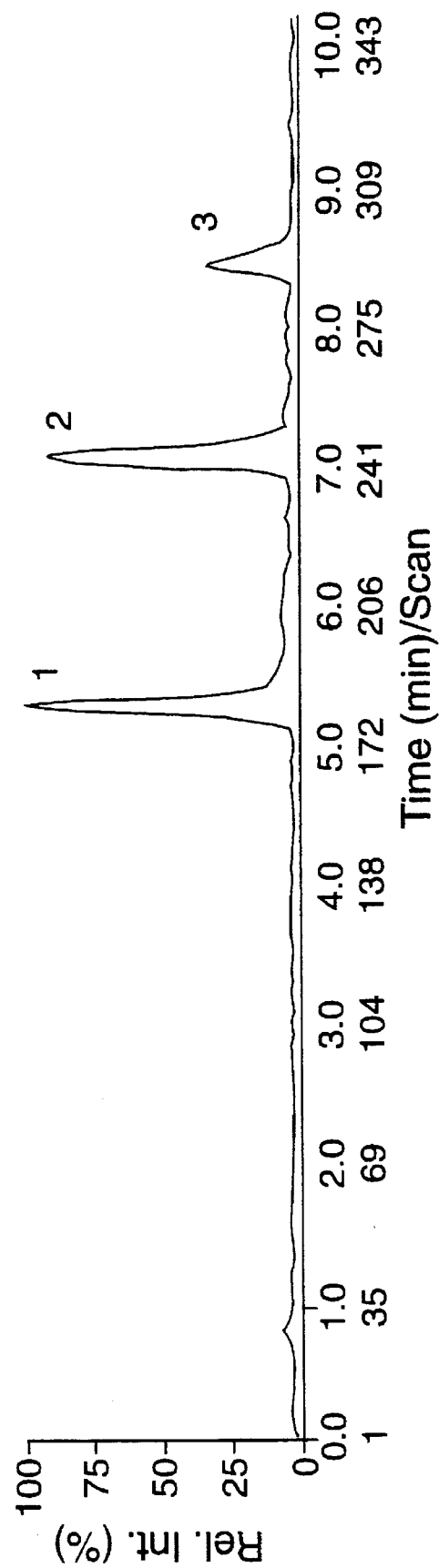
FIGS. 7A, 7B and 7C. Selected positive ion chromatograms of genistein glycosidic conjugates in isolated soy protein (A), toasted soy flour (B), and defatted soy flour (C) following HPLC-APCI-HN analysis on a 10 cm×4.6 mm $C_8$ Aquapore reversed-phase column. The chromatograms were obtained from the sum of the 519, 475 and 433 m/z ions. The mobile phase was a 0–50% acetonitrile gradient over 10 min in 2 mM ammonium acetate at a flow rate of 1 ml/min. Peak identification: 1=genistein 6-OMalGlc, 2=genistin, 3=genistein 6-OAcGlc. The individual analyses were performed over a six month period, accounting for the small differences in retention times.
Figure 7B:
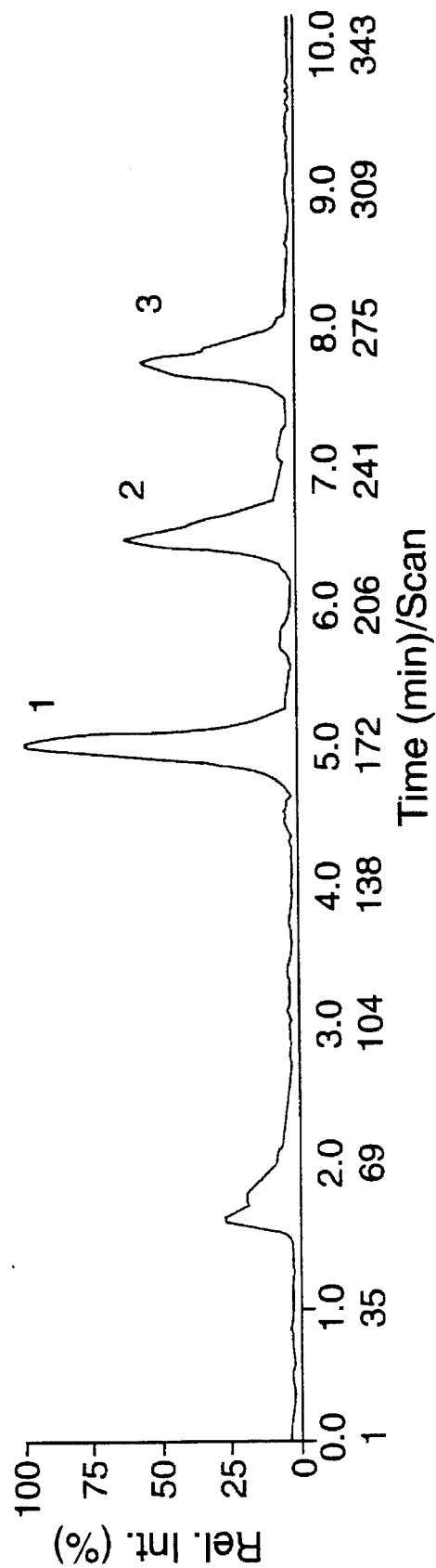
Figure 7C:
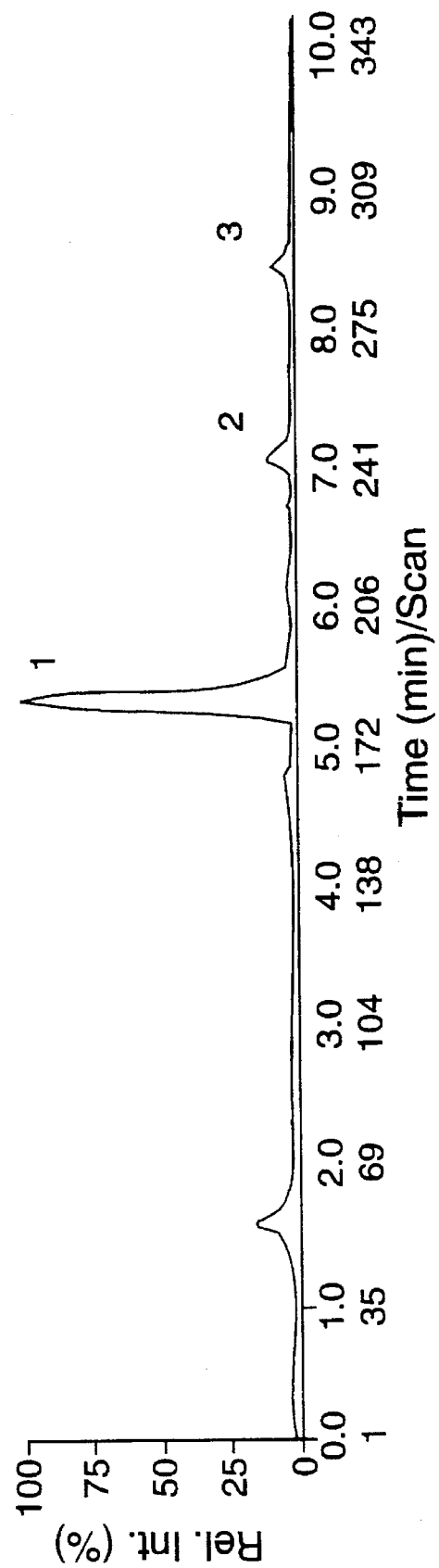
Figure 8A:
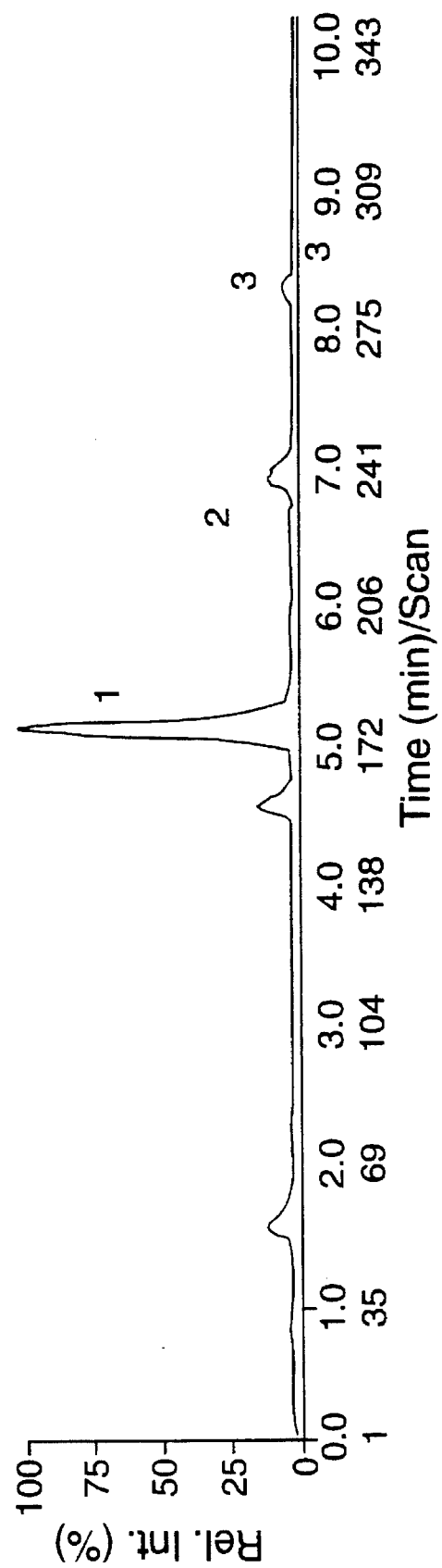
FIGS. 8A, 8B and 8C. Selected positive ion chromatograms of genistein glycosidic conjugates in soybean hypocotyl (A), tofu (B) and soy molasses (C) following HPLC-APCI-HN analysis on a 10 cm×4.6 mm $C_8$ Aquapore reversed-phase column. The ions selected to generate the chromatograms.
Figure 8B:
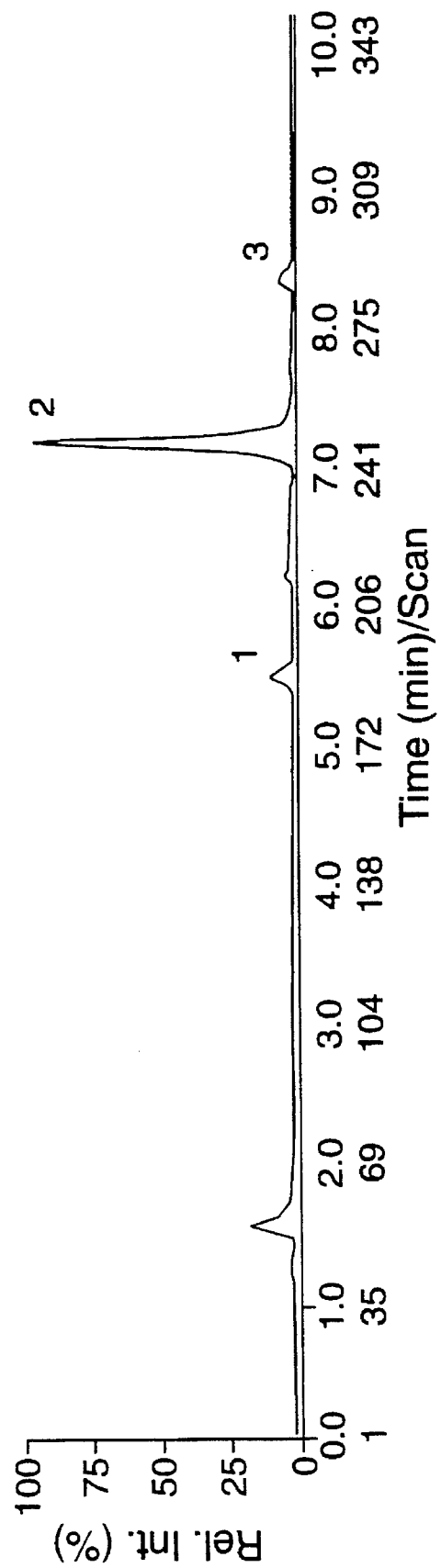
Figure 8C:
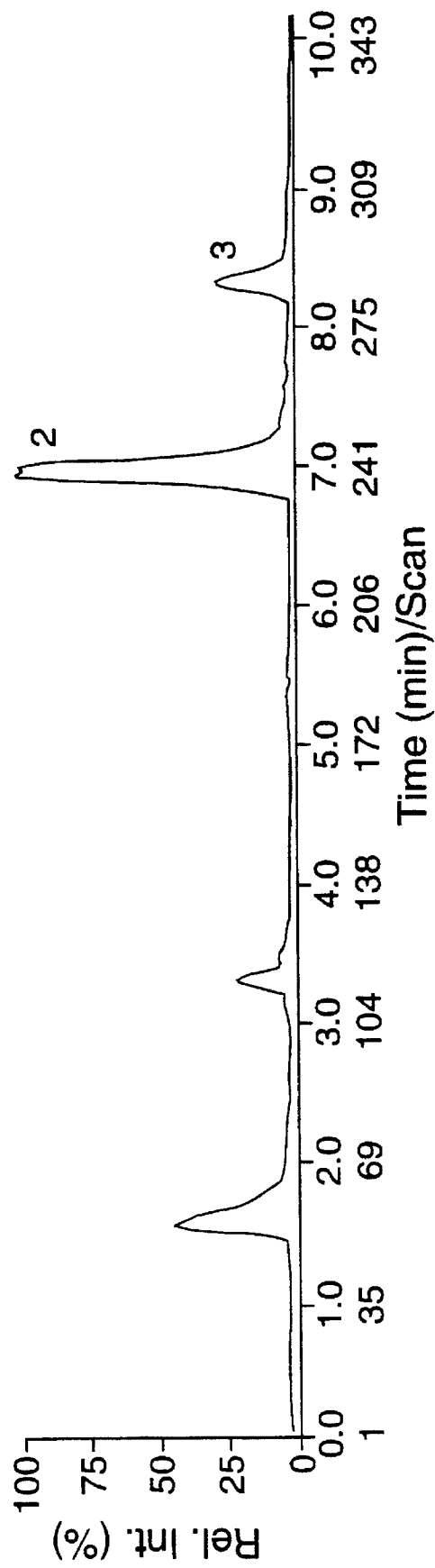

*Mean ± SD of triplicate measurements
[a]Significantly different (p <0.05) from 1 hr room temperature extraction
[b]Significantly different (p <0.05) from 2 hr room temperature extraction
[c]Significantly different (p <0.05) from 24 hr room temperature extraction 2. HPLC-Mass spectrometry When analyzed by HPLC-HN-APCI mass spectrometry in the positive ion mode, three different types of conjugates were identified for each isoflavone. In the case of defatted soy flour (FIG. 7) and soybean hypocotyls (FIG. 8), the principal conjugate was the 6-OMalGlc of each of the three isoflavones, daidzein (7,4'-dihydroxyisoflavone), genistein and glycitein (7,4'-dihydroxy-6-methoxyisoflavone). In contrast, in soy molasses and tofu, the principal conjugates were the isoflavone bglucosides (FIG. 8). Toasted soy flour and the isolated soy protein contained large amounts of the 6-OAcGlc conjugates (FIG. 7).

Figure 9A:
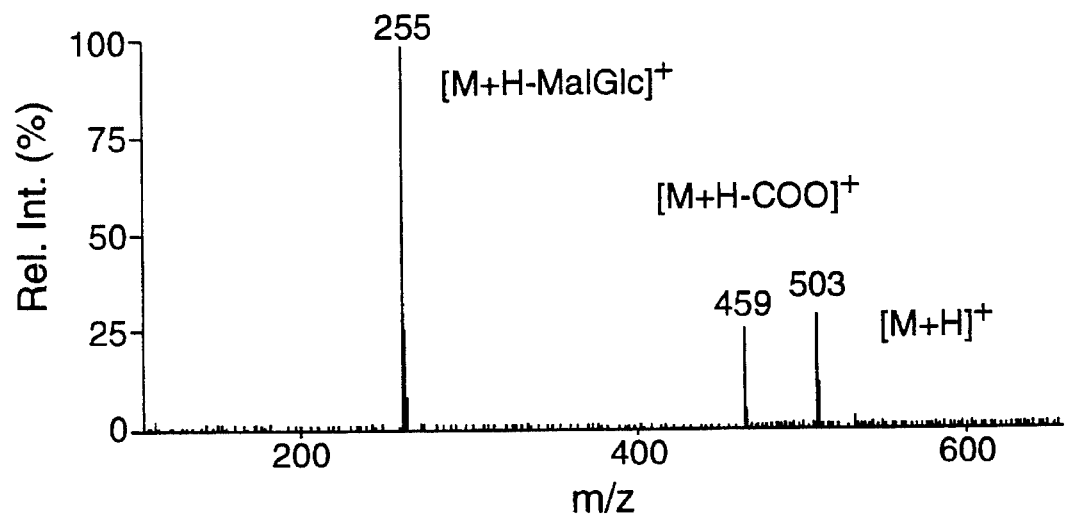
FIGS. 9A, 9B and 9C. Positive ion mass spectra of daidzein (A), genistein (B), and glycitein (C) 6-OMalGlc conjugates in isolated soy protein separated by reversed-phase HPLC.
Figure 9B:
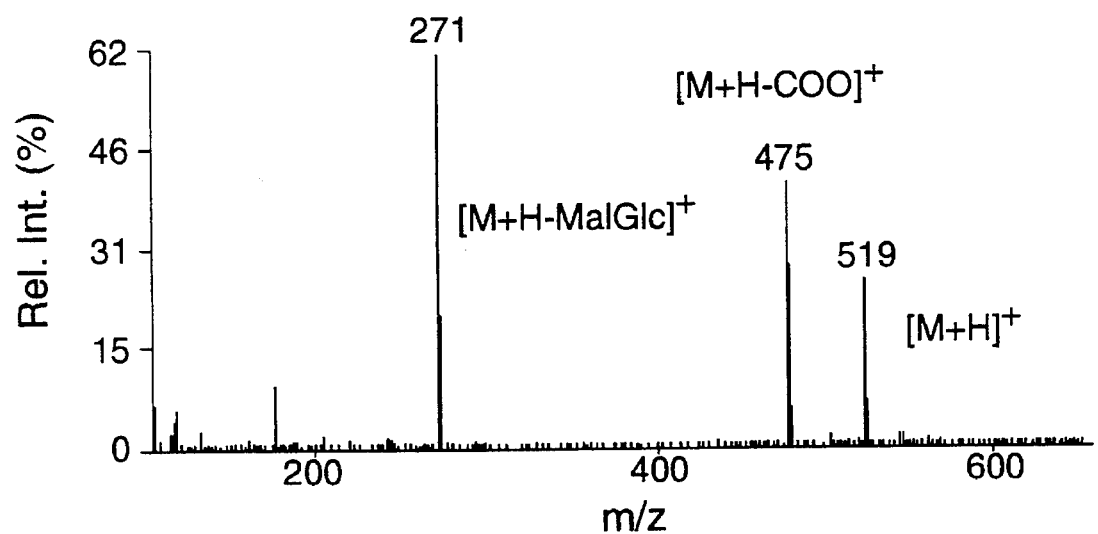
Figure 9C:
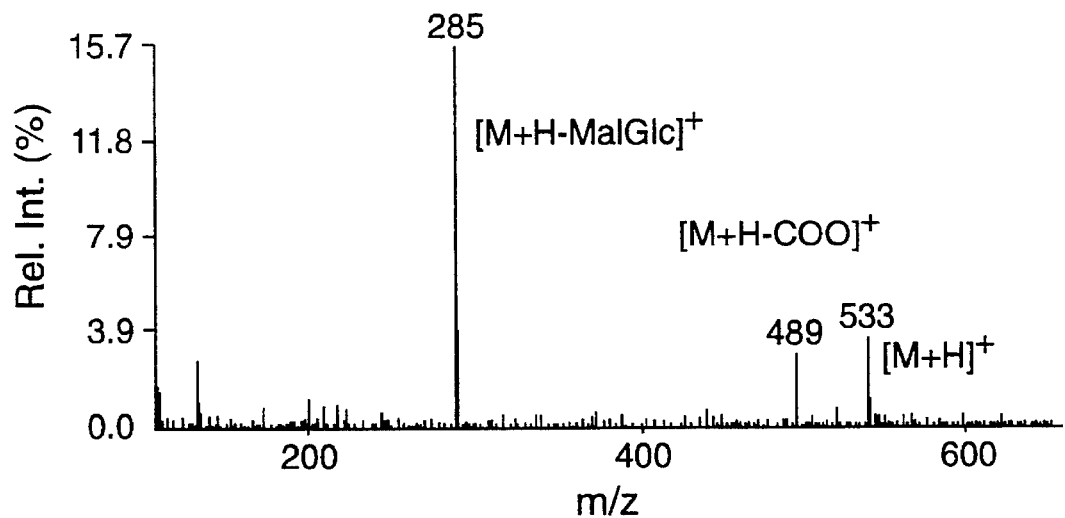

Isoflavone 6-OMalGlc conjugates The major ions in the HN-APCI positive ion mass spectrum of each isoflavone 6-OMalGlc conjugate when analyzed by HPLC in a background of 0.1% acetic acid (FIG. 9) were the [M+H]$^+$ molecular ion, the [M+H–COO]$^+$ ion and the [M+H–MalGlc]$^+$ aglucone ion. However, when analyzed by HPLC in a background of 10 mM ammonium acetate, the molecular ion was not observed.

In the negative ion mode, whether analyzed by HPLC in 0.1% acetic acid or in 10 mM ammonium acetate, the molecular [M–H]⁻ ion for each isoflavone 6-OMalGlc was not observed. Instead, the [M–MalGlc–H]⁻ aglucone ion was the principal ion. The other major ions were the [M–COOH]⁻ ion and the [M–COOH+Acetic acid]⁻ adduct ion. At high orifice potential (–100 V vs –60 V), the adduct ions were not detected.

Positive ion mass spectra for each isoflavone 6-OMalGlc obtained with the IonSpray™ interface showed that under these conditions (no heating) the intact [M+H]⁺ molecular ion was the most abundant. Other major ions were ammonium and potassium adducts with the molecular ion ([M+NH$_4$]⁺, [M+K]⁺ and [M+2K]⁺ ions) and the aglucone ion [MMalGlc]⁺. In the negative ion mode, the molecular [M–H]⁻ ion was the most abundant ion. Other major ions were the acetic acid adduct [M–H+acetic acid]⁻, [M–COOH]⁻, and the aglucone ion [M–H–MalGlc]⁻.

Figure 10A:
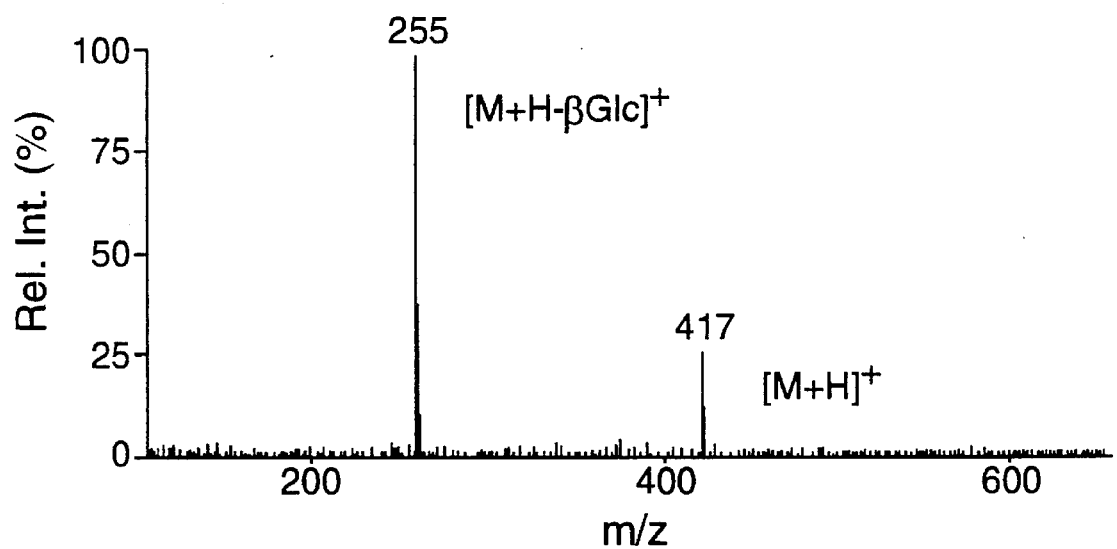
FIGS. 10A, 10B and 10C. Positive ion mass spectra of daidzin (A), genistin (B), and glycitin (C) in isolated soy protein separated by reversed-phase HPLC.
Figure 10B:
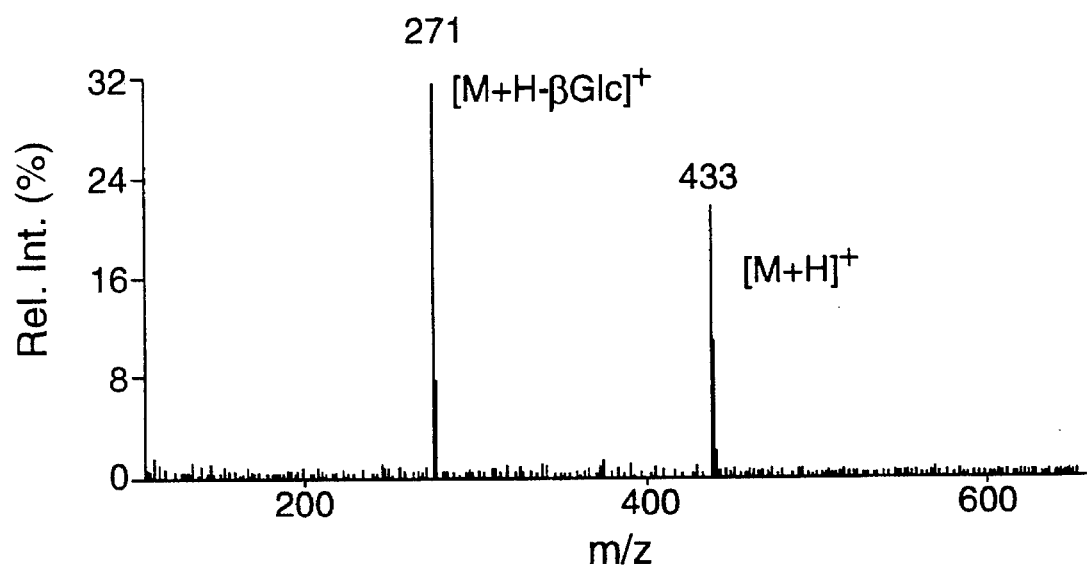
Figure 10C:
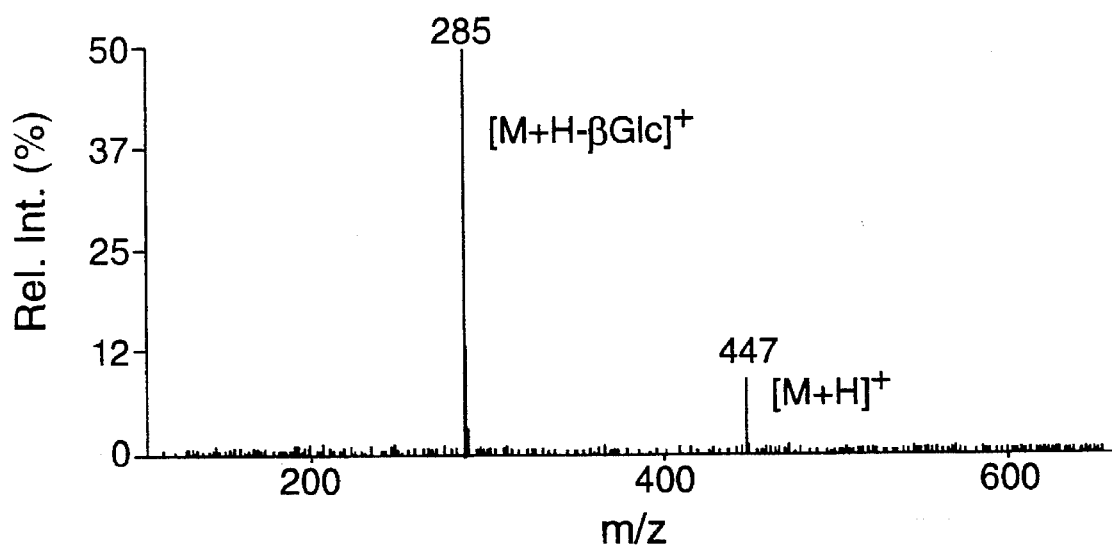

Isoflavone b-glucoside conjugates Daidzin, genistin and glycitin gave rise to two main ions using the HN-APCI interface, the molecular [M+H]⁺ ion and the [M–Glc+H]⁺ ion (FIG. 10). Corresponding ions [M–H]⁻ and [M–Glc–H]⁻ were observed in negative ion mass spectra. At an orifice potential of –70 V, the acetic acid adduct ions [M–H+acetic acid] were observed. Using the IonSpray™ interface, the molecular ions [M+H]⁺ and [M–H]⁻ were the most abundant ions in positive and negative ion spectra, respectively. The other ions in the positive ion spectra were the potassium adduct ion [M+K]⁺ and the aglucone ion [M+H–Glc]⁺. In the negative ion spectra, the acetate adduct ion [M–H+CH$_3$COO]⁻ and the aglucone ion [M–H–Glc]⁻ were observed.

Figure 11A:
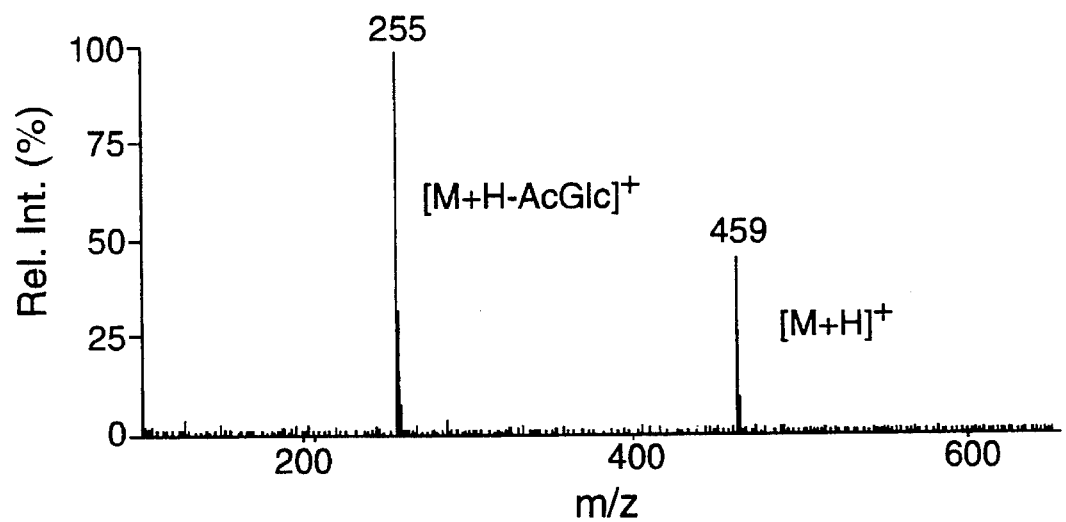
FIGS. 11A, 11B and 11C. Positive ion mass spectra of 6-OAcGlc conjugates of daidzein (A), genistein (B), and glycitein (C) in isolated soy protein separated by reversed-phase HPLC.
Figure 11B:
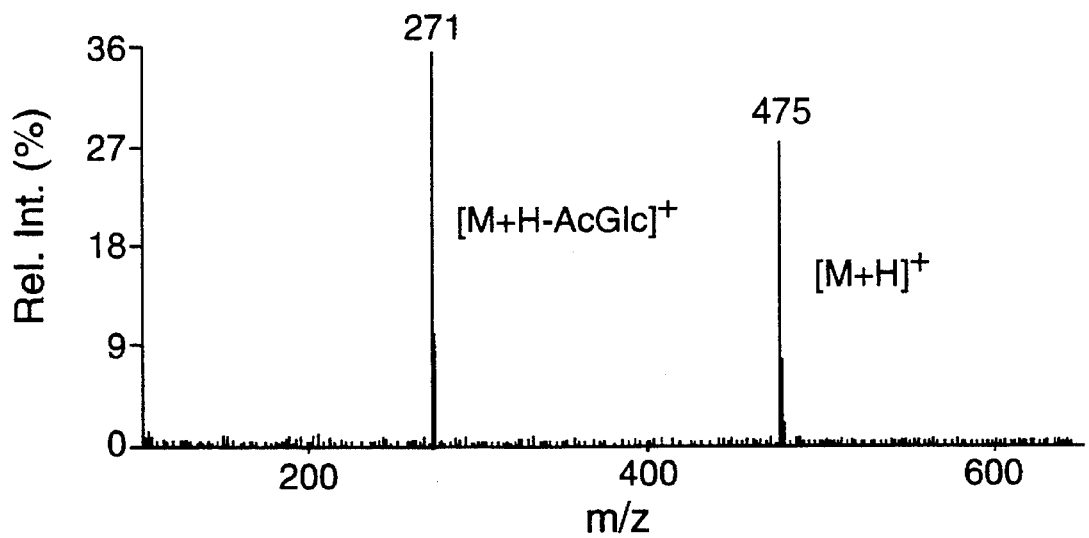
Figure 11C:
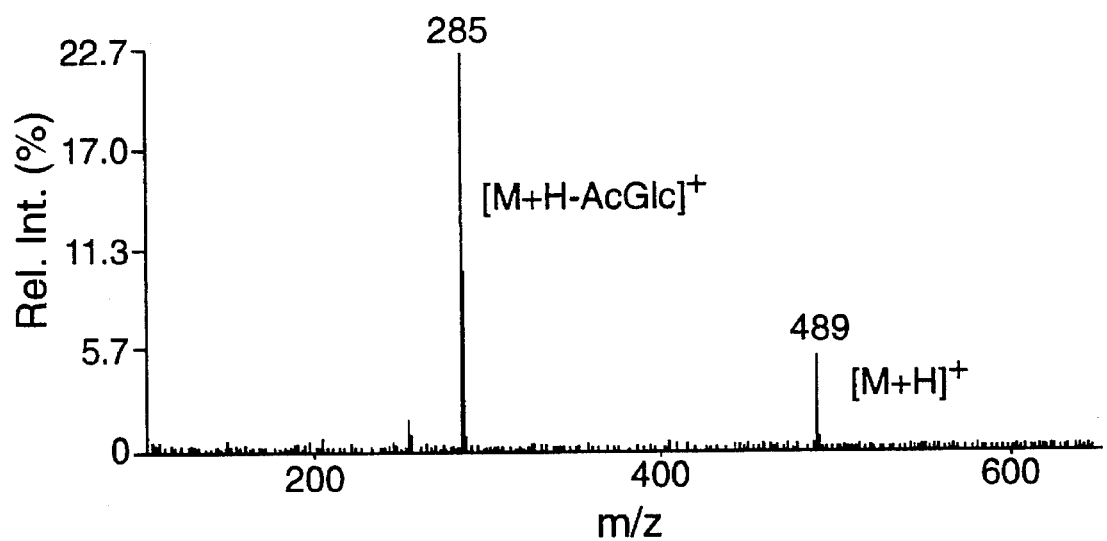

Isoflavone 6-OAcGlc conjugates These conjugates were the least abundant of the conjugates in all soy fractions tested although significant amounts were detected in the toasted soy flour and the isolated soy protein. In the soybean hypocotyl and defatted soy flour they were hardly detectable when using cold solvent extraction. They were also the least mobile of the glycosidic conjugates by HPLC in the presence of ammonium acetate. Using the heated nebulizer-APCI interface, they gave rise in the positive spectra to the molecular ion [M+H]⁺ and the [M–AcGlc+H]⁺ ion, the latter being the most abundant (FIG. 11). Corresponding ions were observed in the negative ion spectra; again, when using an orifice potential of –70 V, an acetic acid adduct with the molecular ion was observed. Using the IonSpray™ interface, the molecular ions [M+H]⁺ and [M–H]⁻ were the most abundant ions in positive and negative ion spectra, respectively. Other major ions in positive ion spectra were the potassium adduct [M+K]⁺ and the aglucone ion [M+H–AcGlc]⁺, whereas in negative ion spectra only the acetate adduct [M–H+CH$_3$COO]⁻ was observed. In the case of genistein 6-OAcGlc, the acetate adduct ion was the most abundant ion.

The relative sensitivity of HN-APCI and IonSpray™ for the detection of isoflavone glycosidic conjugates by HPLC-MS was assessed using a 80% aqueous methanol extract of toasted soy flour. The highest sensitivity for each type of conjugate was observed for the positive isoflavone aglucone ions (m/z values, 255, 271 and 285) generated in the HN-APCI interface. They were mostly 1.5 to 3-fold more intense than the positive molecular ions [M+H]⁺ generated in the IonSpray™ interface. The most abundant negative ions generated in the IonSpray™ interface tended to be less intense than their positive counterparts.

3. Isoflavone conjugate intestinal hydrolysis and absorption

The inventors also found that the chemical form of genistein will affect the sites of absorption from the intestines. Unconjugated genistein is fully protonated under the acid conditions of the stomach and would be transported by passive diffusion from the lumen into the tissues in both the stomach and upper small intestine. This is analogous to the absorption of the common drug acetaminophen (tylenol).

The conjugated forms of genistein are not absorbed by passive absorption and therefore must undergo hydrolysis to release the unconjugated genistein. Their hydrolysis does not occur under the acid conditions of the stomach, but instead requires the action of specific enzymes.

In the case of β-glucosides, the β-glucosidase activity of the small intestine is sufficient for substantial hydrolysis to occur there, leading to the appearance of isoflavones in the blood which peak at 2 hours. This is consistent with absorption occurring in the small intestine. The inventors have observed this in clinical studies in which the full-fat soy milk (containing almost exclusively β-glucosides) was consumed.

The modified β-glucosides, the 6"-O-acetylglucosides and the 6"-O-malonylglucosides, are poor substrates for the β-glucosidases present in the small intestine, consistent with the report that the 6"-O-acetylglucosides are not hydrolyzed by β-glucosidase (Farmakalids & Murphy, 1985). In addition, the inventors have found that when volunteers (5) consumed a soy protein beverage (Supro) rich in the 6"-O-acetylglucosides and the 6"-O-malonylglucosides, isoflavones did not appear in the blood and urine for 4–8 hours afterwards (unlike full-fat soy milk where blood levels peaked at 2 hours after ingestion). Finally, the search for tyrosine kinase inhibitors formed by microorganisms led to the discovery of genistein. Genistein was not synthesized by the microorganisms, but rather released by hydrolysis of the 6"-O-malonylglucosides in the soymeal used as a source of protein for the growth of the microorganisms. The organisms associated with the appearance of genistein in the growth media were those normally found in the large bowel.

As part of their enterohepatic circulation, isoflavones are glucuronidated. The isoflavone glucuronides, as for other glucuronides, are hydrolyzed by β-glucuronidases in the large bowel, and the unconjugated forms reabsorbed. In this environment they may undergo other chemical modifications, such as reduction to isoflavans or B-ring-opened forms.

C. Discussion

In the present example, it has been shown that the extraction of isoflavone conjugates from the soy matrices tested occurs readily at room temperature in 80% aqueous methanol, being essentially complete within 1–2 hr. Heating, as used by many previous investigators, is unnecessary and, as noted above, alters the isoflavone composition. However at 60° C., the magnitude of the heat-induced changes was considerably less than at 80° C.

Farmakalidis & Murphy (1985) suggested that 80% aqueous methanol was not as good an extractant of 6-OAcGlc conjugates compared to 80% aqueous acetonitrile-0.1% HCl. However, data in this study show that these two solvents were equally good when used at room temperature. When extraction was carried out with 80% aqueous methanol at 80° C. for 1–4 h, the concentration of the isoflavone 6-OMalGlc conjugates and 6OAcGlc conjugates (in toasted soy flour) declined as the β-glucoside conjugates rose. The de-esterification reaction was presumably a result of trans-esterification of the ester linkage between the malonate or acetate carboxyl group and the 6"-hydroxyl group of the glucose moiety, yielding methyl malonate or methyl acetate and the isoflavone β-glucoside. This effect may explain the apparently lower concentrations of isoflavone 6-OAcGlc conjugates in 80% aqueous methanol extracts of toasted soy flour, as reported previously (Farmakalidis & Murphy, 1985). It should be noted that storage of extracts for extended periods even at room temperature would be expected to lead to gradual changes in the composition of isoflavone conjugates.

This example also shows that an important source of the observed variation in isoflavone conjugate composition of different soy foods is the degree of heating the soy material is exposed to during its preparation. Isoflavone 6-OMalGlc conjugates are prone to both heat-induced decarboxylation (to form 6-OAcGlc conjugates) and de-esterification (to form β-glucoside conjugates) (Kudou et al., 1991; Farmakalidis & Murphy, 1985). Thus, soy foods prepared with a aqueous heating step, i.e., pressurized boiling water extraction to prepare full fat soy milk, have a marked reduction of 6-OMalGlc conjugates compared to whole soybeans and to products in which heating was minimized. In the case of soy milk, soy molasses, a concentrate of a hot 65% aqueous ethanol extract of soy flour, and tofu essentially complete de-esterification to the β-glucosides was the principal chemical change. Indeed, the predominance of the β-glucosides over other isoflavone conjugates in soy molasses has enabled investigators to isolate genistin (the β-glucoside of genistein) on a large scale from this matrix (Barnes et al., 1994; Coward et al., 1993; Walter, 1941).

Since the isoflavone 6-OAcGlc conjugates are virtually absent from extracts of the soybean cotyledon and hypocotyl, but are present in large quantities in toasted soy flour and to a lesser extent in the isolated soy protein, it is apparent that they are formed during the drying process used to manufacture the latter products.

The present example also describes for the first time the application of HPLC-mass spectrometry with HN-APCI and IonSpray™ interfaces to the analysis of isoflavones. Isoflavones in soy foods are more readily detected using the aglucone ions generated in the HN-APCI interface than molecular ions or their adducts generated in the IonSpray™ interface.

The data confirm findings that, in addition to the β-glucoside conjugates, isoflavones in soy hypocotyl and cotyledon are also present as 6-OMalGlc conjugates (Kudou et al., 1991) and in toasted soy flour as 6-OAcGlc conjugates (Farmakalidis & Murphy, 1985). Even though the 6-OMalGlc conjugates contain a carboxylic acid group, positive ion mass spectra obtained with the HN-APCI interface were easier to interpret than negative ion mass spectra. The molecular $[M+H]^+$ ion was a prominent ion in the positive ion mass spectra when HPLC analysis was conducted in a background of acetic acid, but not in a background of ammonium acetate. In contrast, the $[M-H]^-$ ion was absent in the negative ion mass spectra when HPLC analysis was conducted in a background of acetic acid or ammonium acetate. This suggests that the carboxylate ion more readily decarboxylates in the heated nebulizer than the protonated carboxylic acid.

The isoflavone b-glucosides and 6-OAcGlc conjugates yielded molecular ions in both positive and negative ion mass spectra, but the most abundant ion in each case was the aglucone ion. Therefore, to identify the conjugates of an isoflavone in serial mass spectra obtained following reversed-phase HPLC separation of food extracts, selected ion chromatograms were prepared with a combination of the aglucone ion and the molecular ions of the individual conjugates. This was important for conjugates of glycitein since their mass spectra contained a much lower relative abundance of the molecular ion compared with daidzein and genistein conjugates.

Introduction of isoflavone β-glucoside and 6-OAcGlc ions into the mass spectrometer via the IonSpray™ interface resulted in a lower sensitivity than using the HN-APCI interface. However, since sensitivity in the IonSpray™ interface is dependent on concentration of the solute in the nebulized droplets rather the amount of solute (as observed in the HN-APCI interface), the use of a capillary HPLC column, as used in the analysis of peptide digests, would markedly increase sensitivity in this mode. For example, in the case of a 0.3 mm i.d. capillary column, the theoretical improvement in sensitivity would be 50-fold.

In contrast to the HN-APCI interface, the molecular ions of the 6-OMalGlc conjugates were the most abundant in both positive and negative ion mass spectra, probably since the sample was not heated (and minimally decarboxylated) before it entered the mass spectrometer. The b-glucosides and the 6OAcGlc conjugates, not having a carboxylic acid group, readily formed adducts with the acetate ion, these ions being the most abundant in negative ion mass spectra. The extent to which this happened was reduced by increasing the orifice potential. The relative molar ion yields for the three types of conjugates and the three isoflavones varied only over a two fold range and were similar in positive and negative ion mass spectra.

The inventors also found that the 6"-O-substitution has an effect on the susceptibility of the isoflavone conjugates to intestinal hydrolysis and hence absorption. There are thus differences in bioavailability and metabolism of the isoflavones dependent on the nature of their chemical form.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the composition, methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Adlercreutz H., Fotsis, T., Lampe J., Wähälä K., Mäkelä T., Brunow G. & Hase T., *Scand J Clin Lab Invest*, 53 (suppl 215): 5–18, 1993.

Adlercreutz; International Symposium on Phytoestrogens; Little Rock, Ark., Oct. 17–20th, 1993; Proceedings published in *Proc. Soc. Exptl. Biol. Med.*

Akiyama et al., *J. Biol. Chem.*, 262 (12):5592–5595, 1987.

Bekker, P. J., and Gay, C. V. *J. Bone Min. Res.*, 5:569–576, 1990.

Barnes S, Peterson T. G., Grubbs C., Setchell K. D. R. *In Diet and Cancer: Markers, Prevention and Treatment*, M. Jacobs, ed., Plenum Press, New York, 135–148, 1994.

Blair, H. C., Kahn, A. J., Crouch, E. C., Jeffrey, J. J., and Teitelbaum, S. I., *J. Cell Biol.*, 102:1164–1172, 1986.

Blair, H. C., Teitelbaum, S. L., Ghiselli, R., and Gluck, S., *Science*, 245:855–857, 1989.

Blair, H. C., and Schlesinger, P. H., *Biochem. Biophys. Res. Comm.*, 171:920–925, 1990.

Blair, H., Teitelbaum, S. L., Tan. H.-L., Koziol, C. M., and Schlesinger, P. H., *Am. J. Physiol.* 260 (Cell Physiol. 29):C1315–C1324, 1991.

Blair, H. C., and Schlesinger, P. H. In: *The Biology and Physiology of the Osteoclast*, CRC Press, Eds., Gay, C. V. and Rifkin, B. R. pp 259–288, 1992.

Brandi, M. L., *Bone Miner* 19(suppl):S3–S14, 1992.

Breslau, N. A., Brinkley, L., Hill, K. D., and Pak, C. Y. C. *J. Clin. Endocrinol. Metab.* 66:140–146.1988.

Carano, A., Teitelbaum, S. L., Konsek, J. D., Schlesinger, P. H., and Blair, H. C., *J. Clin. Invest.*, 85:456–461, 1990.

Carroll, *J. Amer. Diet. Assoc.* 91:820–827, 1992.

Coward et al., *J Agric Food Sci,* 41, 1961–1967, 1993.

Davidai et al., *Amer. J. Physiol.* 263:E205–E209,1992.

Eldridge, *J. Agric. Food Chem.*, 31:394–396,1982.

Farmakalidis E, Murphy P. A. *J Agric Food Chem* 33, 385–389, 1985.

Kallman, *LET'S LIVE,* 12, May, 1994.

Kalu et al., *Endocrinology,* 122:1847–1854, 1988.

Kudou S., Fleury Y., Welti D., Magnolato D., Uchida T., Kitamura K., Okubo K. *Agric Biol Chem,* 55, 2227–2233, 1991.

Messina, M. J., Persky, V., Setchell, K. D. R. & Barnes, S. *Nutr. Cancer,* 21, 113–131, 1994.

Murphy, P.A. *Food Technol.* 36:60–64, 1982.

Quarles et al., *Endocrinology* 132:1505–1513, 1993.

Schlesinger, P. H. and Blair, H. C. In: *The Biology and Physiology of the Osteoclast*, CRC Press, Editor: Eds., Gay, C. V. and Rifkin, B. R. pp 259–288, 1992.

Schvartz, I., Ittop, O., Davidai, G., Hazum, E. *Peptides* 13:159–163, 1992.

Setchell; International Symposium on Phytoestrogens; Little Rock, Ark., Oct. 17–20th, 1993; Proceedings published in *Proc. Soc. Exptl. Biol. Med.*

Soyatech Survey and Estimates, P.O. Box 84, Bar Harbor Me. and Soyfoods Center Survey, P.O. Box 234, Lafayette, Calif.

Soybean Utilization, Eds. Snyder, H. E. and Kwon, T. W., Van Nostrand, New York, p.220.

Väänänen, H. K., Karhukorpi, E. -K., Sundquist, K. Wallmark, B., Roininen, I., Hentunen, T., Tuukkanen, J., and Lakkakorpi, P., *J. Cell Biology,* 111:1305–1311, 1990.

Walter, E. D. *J Am Oil Chem Soc,* 63, 3273–3276, 1941.

Yoneda et al. *J. Clin. Invest.* 91:2791–2795, 1993.

Yueh T-L. & Chu H.-Y. *Sci Sinica* 20, 513–522, 1977.

Zambonin-Zallone, A., Teti, A., and Primevera, M. V., *Anatomy and Embryology,* 165:405–412, 1982.

What is claimed is:

1. A method for reducing acid secretion by osteoclasts, comprising contacting an osteoclast with a composition comprising an amount of a genistein-glucoside conjugate that occurs naturally in soy, the amount effective to inhibit osteoclast acid secretion.

2. The method of claim 1, wherein the genistein conjugate is a 6-O"-acetylglucoside conjugate or a 6-O"-malonylglucoside conjugate.

3. The method of claim 1, wherein the genistein conjugate is obtained from soy or a soy product.

4. The method of claim 1, wherein the genistein conjugate is a synthetic form of a genistein conjugate that occurs naturally in soy.

5. The method of claim 1, wherein the osteoclast is located within an animal and the genistein conjugate is administered to said animal in a pharmaceutically acceptable form.

6. The method of claim 5, wherein the genistein conjugate is administered to said animal in the form of a tablet.

7. The method of claim 5, wherein the genistein conjugate is administered to said animal in the form of a soy food product.

8. The method of claim 7, wherein the genistein conjugate is administered to said animal in the form of an unprocessed soy food or isolated soy protein composition.

9. A method for reducing bone resorption, comprising administering to an animal exhibiting symptoms associated with bone resorption an amount of a pharmaceutically acceptable composition comprising a genistein-glucoside conjugate that occurs naturally in soy, the amount effective to reduce acid secretion by osteoclasts located within the animal.

10. The method of claim 9, wherein the pharmaceutically acceptable composition comprises a 6-O"-acetylglucoside or 6-O"-malonylglucoside genistein conjugate.

11. The method of claim 9, wherein the pharmaceutically acceptable genistein conjugate composition is administered orally.

12. The method of claim 9, wherein the pharmaceutically acceptable genistein conjugate composition is in the form of a tablet.

13. The method of claim 9, wherein the pharmaceutically acceptable genistein conjugate composition is in the form of a soy food product.

14. The method of claim 13, wherein the soy food product is an unprocessed soy food or isolated soy protein composition.

15. A method for treating osteoporosis, comprising administering to a patient suspected of having osteoporosis a pharmacologically effective amount of a pharmaceutically acceptable genistein-glucoside conjugate composition that occurs naturally in soy.

16. The method of claim 15, wherein the pharmaceutically acceptable genistein conjugate composition comprises a 6-O"-acetylglucoside or 6-O"-malonylglucoside genistein conjugate.

17. The method of claim 16, wherein the pharmaceutically acceptable genistein conjugate composition is in tablet form.

18. The method of claim 17, wherein the pharmaceutically acceptable genistein conjugate composition is a tablet comprising 2–50 mg of the genistein conjugate.

19. The method of claim 18, wherein the pharmaceutically acceptable genistein conjugate composition is a tablet comprising 5–50 mg of the genistein conjugate.

20. The method of claim 19, wherein the pharmaceutically acceptable genistein conjugate composition is a tablet comprising 10–50 mg of the genistein conjugate.

21. The method of claim 20, wherein the pharmaceutically acceptable genistein conjugate composition is a tablet comprising 20–50 mg of the genistein conjugate.

22. The method of claim 21, wherein the pharmaceutically acceptable genistein conjugate composition is a tablet comprising 50 mg of the genistein conjugate.

23. The method of claim 16, wherein the pharmaceutically acceptable genistein conjugate composition is a soy food product.

24. The method of claim 23, wherein the pharmaceutically acceptable genistein conjugate composition is 2–50 mg of isolated soy protein or unprocessed soy food.

25. The method of claim 24, wherein the pharmaceutically acceptable genistein conjugate composition is 5–50 mg of isolated soy protein or unprocessed soy food.

26. The method of claim 25, wherein the pharmaceutically acceptable genistein conjugate composition is 10–50 mg of isolated soy protein or unprocessed soy food.

27. The method of claim 26, wherein the pharmaceutically acceptable genistein conjugate composition is 20–50 mg of isolated soy protein or unprocessed soy food.

* * * * *

UNITED STATES PATENT AND TRADEMARK OFFICE
CERTIFICATE OF CORRECTION

PATENT NO. : 5,506,211
DATED : April 9, 1996
INVENTOR(S) : Barnes, et al

It is certified that error appears in the above-indentified patent and that said Letters Patent is hereby corrected as shown below:

On the title page: Item [54] and Column 1, line 2, should read -- GENISTEIN FOR USE IN INHIBITING OSTEOCLASTS --.

Signed and Sealed this

Fifteenth Day of October, 1996

Attest:

BRUCE LEHMAN

*Attesting Officer*  *Commissioner of Patents and Trademarks*